(12) United States Patent
Hundertmark et al.

(10) Patent No.: US 11,832,804 B2
(45) Date of Patent: Dec. 5, 2023

(54) APPARATUS AND METHOD FOR SEALING A VASCULAR PUNCTURE

(71) Applicant: ACCESS CLOSURE, INC., Santa Clara, CA (US)

(72) Inventors: Ronald Ray Hundertmark, San Mateo, CA (US); Kevin To, San Jose, CA (US); Curt Guyer, Dublin, CA (US); Rick Repp, San Jose, CA (US); Martin Schnitzer, San Francisco, CA (US); Sravanthi Avuthu, Portola Valley, CA (US)

(73) Assignee: ACCESS CLOSURE, INC., Santa Clara, CA (US)

( * ) Notice: Subject to any disclaimer, the term of this patent is extended or adjusted under 35 U.S.C. 154(b) by 750 days.

(21) Appl. No.: 16/662,809

(22) Filed: Oct. 24, 2019

(65) Prior Publication Data
US 2020/0054313 A1    Feb. 20, 2020

Related U.S. Application Data

(63) Continuation of application No. 14/941,222, filed on Nov. 13, 2015, now Pat. No. 10,456,123.
(Continued)

(51) Int. Cl.
*A61B 17/00*    (2006.01)

(52) U.S. Cl.
CPC .... *A61B 17/0057* (2013.01); *A61B 17/00234* (2013.01); *A61B 17/00491* (2013.01);
(Continued)

(58) Field of Classification Search
CPC ........ A61B 17/0057; A61B 2017/0065; A61B 2017/00654; A61B 2017/0046;
(Continued)

(56) References Cited

U.S. PATENT DOCUMENTS

| 378,939 A | 3/1888 | Smith et al. |
| 5,545,133 A | 8/1996 | Burns et al. |

(Continued)

FOREIGN PATENT DOCUMENTS

| CN | 306873583 | 10/2021 |
| EP | 0835076 A1 | 4/1998 |

(Continued)

OTHER PUBLICATIONS

Accessclosure [Online], [retrieved on May 31, 2018]. Retrieved from the Internet:>http://accessclosure.com/newsite/products/mynx-ace/.

(Continued)

*Primary Examiner* — Melanie R Tyson
(74) *Attorney, Agent, or Firm* — ARENTFOX SCHIFF LLP

(57) ABSTRACT

A closure system for delivering a sealant to an arteriotomy. A distal section of the closure system can include overlapping inner and outer sleeves that can expand with expansion of the sealant. A proximal section of the closure system can include a handle portion and a sheath adapter extending from the handle portion. The handle portion can comprise one or more actuators that when depressed or engaged can assist in deployment of the sealant in the arteriotomy and can further include tamping of the sealant and/or retraction of an expandable member. The sheath adapter can removably engage a side port or an irrigation line of a standard procedural sheath. When the sheath adapter is secured to the procedural sheath, movement of the closure system can also move the procedural sheath.

12 Claims, 34 Drawing Sheets

Related U.S. Application Data

(60) Provisional application No. 62/079,878, filed on Nov. 14, 2014.

(52) U.S. Cl.
CPC .......... *A61B 2017/0046* (2013.01); *A61B 2017/0065* (2013.01); *A61B 2017/00238* (2013.01); *A61B 2017/00654* (2013.01); *A61B 2017/00898* (2013.01)

(58) Field of Classification Search
CPC .......... A61B 2017/00367; A61B 2017/00371; A61B 2017/00389
See application file for complete search history.

(56) References Cited

U.S. PATENT DOCUMENTS

| | | |
|---|---|---|
| D378,939 S | 4/1997 | Smith et al. |
| 5,951,589 A | 9/1999 | Epstein et al. |
| 6,045,570 A | 4/2000 | Epstein et al. |
| 6,056,768 A | 5/2000 | Cates et al. |
| 6,056,769 A | 5/2000 | Epstein et al. |
| 6,056,770 A | 5/2000 | Epstein et al. |
| 6,090,130 A | 7/2000 | Nash et al. |
| 6,162,240 A | 12/2000 | Cates et al. |
| 6,179,863 B1 | 1/2001 | Kensey et al. |
| 6,197,042 B1 | 3/2001 | Ginn et al. |
| 6,334,865 B1 | 1/2002 | Redmond et al. |
| 6,391,048 B1 | 5/2002 | Ginn et al. |
| 6,461,364 B1 | 10/2002 | Ginn et al. |
| 6,569,185 B2 | 5/2003 | Ungs |
| D483,475 S | 12/2003 | Kirwan et al. |
| 6,699,261 B1 | 3/2004 | Cates et al. |
| 6,699,262 B2 | 3/2004 | Redmond et al. |
| 6,818,008 B1 | 11/2004 | Cates et al. |
| 6,896,692 B2 | 5/2005 | Ginn et al. |
| 6,929,655 B2 | 8/2005 | Egnelov et al. |
| 6,949,114 B2 | 9/2005 | Milo et al. |
| 7,250,057 B2 | 7/2007 | Forsberg et al. |
| D551,344 S | 9/2007 | Santora, Jr. |
| D560,805 S | 1/2008 | Young et al. |
| 7,316,704 B2 | 1/2008 | Bagaoisan |
| 7,331,979 B2 | 2/2008 | Khosravi et al. |
| 7,331,981 B2 | 2/2008 | Cates et al. |
| 7,335,220 B2 | 2/2008 | Khosravi et al. |
| 7,335,330 B2 | 2/2008 | Odaka |
| 7,361,183 B2 | 4/2008 | Ginn |
| D595,421 S | 6/2009 | Suzuki |
| 7,597,705 B2 | 10/2009 | Forsberg et al. |
| 7,618,436 B2 | 11/2009 | Forsberg et al. |
| 7,618,438 B2 | 11/2009 | White et al. |
| 7,691,127 B2 | 4/2010 | Yassinzadeh |
| 7,806,856 B2 | 10/2010 | Bagaoisan et al. |
| 7,837,705 B2 | 11/2010 | White et al. |
| 7,931,669 B2 | 4/2011 | Ginn et al. |
| 7,931,670 B2 | 4/2011 | Fiehler et al. |
| 7,988,706 B2 | 8/2011 | Forsberg et al. |
| 7,993,367 B2 | 8/2011 | Bagaoisan et al. |
| 8,002,742 B2 | 8/2011 | Pai et al. |
| 8,029,533 B2 | 10/2011 | Bagaoisan et al. |
| 8,262,693 B2 | 9/2012 | Pai et al. |
| 8,298,259 B2 | 10/2012 | Terwey |
| 8,317,824 B2 | 11/2012 | Jenson et al. |
| 8,323,305 B2 | 12/2012 | Epstein et al. |
| 8,333,787 B2 | 12/2012 | Pipenhagen et al. |
| 8,382,794 B2 | 2/2013 | Belhe et al. |
| 8,382,795 B2 | 2/2013 | Forsberg et al. |
| 8,382,797 B2 | 2/2013 | Khosravi et al. |
| 8,382,798 B2 | 2/2013 | Khosravi et al. |
| 8,394,122 B2 | 3/2013 | Bagaoisan et al. |
| 8,444,673 B2 | 5/2013 | Thielen et al. |
| 8,465,518 B2 | 6/2013 | Forsberg |
| 8,465,519 B2 | 6/2013 | Terwey |
| 8,506,592 B2 | 8/2013 | Killion et al. |
| 8,529,598 B2 | 9/2013 | Jenson et al. |
| 8,568,445 B2 | 10/2013 | Pipenhagen et al. |
| 8,591,542 B2 | 11/2013 | White et al. |
| 8,617,204 B2 | 12/2013 | Khosravi et al. |
| 8,647,364 B2 | 2/2014 | Fiehler et al. |
| 8,652,166 B2 | 2/2014 | Akerfeldt et al. |
| 8,685,059 B2 | 4/2014 | Walters |
| 8,721,680 B2 | 5/2014 | Hundertmark et al. |
| 8,747,435 B2 | 6/2014 | Yassinzadeh |
| 8,758,402 B2 | 6/2014 | Jenson et al. |
| 8,845,683 B2 | 9/2014 | Killion et al. |
| 8,870,917 B2 | 10/2014 | Walters |
| 8,911,472 B2 | 12/2014 | Yassinzadeh et al. |
| 8,926,655 B2 | 1/2015 | Vidlund et al. |
| 9,050,087 B2 | 6/2015 | Ginn et al. |
| D736,914 S | 8/2015 | Schultz et al. |
| 9,107,646 B2 | 8/2015 | Tegels |
| 9,131,932 B2 | 9/2015 | Tegels |
| 9,179,897 B2 | 11/2015 | Yassinzadeh et al. |
| 9,192,364 B2 | 11/2015 | Terwey |
| 9,226,739 B2 | 1/2016 | Porter et al. |
| D749,732 S | 2/2016 | Canady et al. |
| D749,733 S | 2/2016 | Canady et al. |
| 9,254,346 B2 | 2/2016 | Pipenhagen et al. |
| 9,282,955 B2 | 3/2016 | Jenson et al. |
| 9,289,195 B2 | 3/2016 | Bagaoisan et al. |
| 9,289,197 B2 | 3/2016 | Forsberg |
| D752,868 S | 4/2016 | Mcgarry et al. |
| D753,301 S | 4/2016 | Fiksen et al. |
| 9,301,740 B2 | 4/2016 | Thielen et al. |
| 9,307,967 B2 | 4/2016 | Tegels et al. |
| 9,364,206 B2 | 6/2016 | Bagaoisan et al. |
| D762,303 S | 7/2016 | Jayaraj |
| 9,386,968 B2 | 7/2016 | Uchida et al. |
| D764,184 S | 8/2016 | Paetzel et al. |
| 9,402,606 B2 | 8/2016 | Glazier et al. |
| D765,841 S | 9/2016 | Schuerg |
| D765,842 S | 9/2016 | Schuerg |
| D766,432 S | 9/2016 | Schuerg |
| 9,439,637 B2 | 9/2016 | Yassinzadeh et al. |
| D770,044 S | 10/2016 | Fiksen et al. |
| D770,618 S | 11/2016 | Fiksen et al. |
| 9,480,468 B2 | 11/2016 | Tegels et al. |
| 9,585,645 B2 | 3/2017 | Akerfeldt et al. |
| 9,597,066 B2 | 3/2017 | Yassinzadeh et al. |
| 9,603,589 B2 | 3/2017 | Terwey et al. |
| 9,668,719 B2 | 6/2017 | Tegels et al. |
| D791,485 S | 7/2017 | Mcgarry et al. |
| 9,713,462 B2 | 7/2017 | Bagaoisan et al. |
| D794,192 S | 8/2017 | Schuerg |
| D794,193 S | 8/2017 | Schuerg |
| D794,194 S | 8/2017 | Schuerg |
| 9,757,105 B2 | 9/2017 | Hundertmark et al. |
| 9,801,631 B2 | 10/2017 | Willard et al. |
| 9,801,786 B2 | 10/2017 | Lev |
| 9,820,726 B2 | 11/2017 | Zhou et al. |
| 9,839,417 B2 | 12/2017 | Walters et al. |
| 9,895,144 B2 | 2/2018 | Tegels et al. |
| 9,913,635 B2 | 3/2018 | Pipenhagen et al. |
| 9,949,754 B2 | 4/2018 | Newhauser et al. |
| 10,004,487 B2 | 6/2018 | Porter et al. |
| D827,132 S | 8/2018 | Grosser et al. |
| D827,133 S | 8/2018 | Grosser et al. |
| D828,550 S | 9/2018 | Falleboe et al. |
| D835,782 S | 12/2018 | Matsumoto et al. |
| D843,573 S | 3/2019 | Avuthu |
| D847,988 S | 5/2019 | Schnitzer |
| D865,166 S | 10/2019 | Avuthu |
| D896,372 S | 9/2020 | Julian |
| D919,086 S | 5/2021 | Hezkiahu |
| D956,221 S | 6/2022 | Deblois |
| D964,130 S | 9/2022 | Zimmermann |
| 2002/0077656 A1 | 6/2002 | Ginn et al. |
| 2002/0077657 A1 | 6/2002 | Ginn et al. |
| 2002/0077658 A1 | 6/2002 | Ginn |
| 2003/0023267 A1 | 1/2003 | Ginn |
| 2003/0078616 A1 | 4/2003 | Ginn et al. |
| 2005/0065549 A1 | 3/2005 | Cates et al. |
| 2005/0085854 A1 | 4/2005 | Ginn |

(56) References Cited

U.S. PATENT DOCUMENTS

| | | |
|---|---|---|
| 2005/0267528 A1 | 12/2005 | Ginn et al. |
| 2005/0283193 A1 | 12/2005 | Tullberg et al. |
| 2006/0190037 A1 | 8/2006 | Ginn et al. |
| 2006/0253037 A1 | 11/2006 | Ginn et al. |
| 2007/0010840 A1 | 1/2007 | Rosenthal et al. |
| 2008/0161849 A1 | 7/2008 | Cates et al. |
| 2008/0221615 A1 | 9/2008 | Ginn et al. |
| 2009/0318955 A1 | 12/2009 | Dave et al. |
| 2010/0114156 A1 | 5/2010 | Mehl |
| 2010/0168767 A1 | 7/2010 | Yassinzadeh et al. |
| 2010/0168789 A1 | 7/2010 | Bagaoisan et al. |
| 2010/0292532 A1 | 11/2010 | Kadykowski et al. |
| 2011/0015670 A1 | 1/2011 | Cates et al. |
| 2011/0015671 A1 | 1/2011 | Cates et al. |
| 2011/0054521 A1 | 3/2011 | Ventura et al. |
| 2011/0106147 A1 | 5/2011 | Cates et al. |
| 2012/0053621 A1 | 3/2012 | Bagaoisan et al. |
| 2012/0209323 A1 | 8/2012 | Uchida et al. |
| 2012/0209359 A1* | 8/2012 | Chen ............... A61B 5/411 607/92 |
| 2012/0290001 A1 | 11/2012 | Uchida et al. |
| 2013/0060279 A1 | 3/2013 | Yassinzadeh |
| 2013/0131718 A1 | 5/2013 | Jenson et al. |
| 2013/0150884 A1 | 6/2013 | Belhe et al. |
| 2013/0190813 A1 | 7/2013 | Tegels et al. |
| 2013/0226229 A1 | 8/2013 | Uchida et al. |
| 2013/0231701 A1 | 9/2013 | Voss et al. |
| 2013/0253579 A1* | 9/2013 | Hundertmark ..... A61B 17/0057 606/214 |
| 2013/0289392 A1 | 10/2013 | Patel et al. |
| 2014/0025103 A1 | 1/2014 | Hundertmark et al. |
| 2014/0135826 A1 | 5/2014 | Tegels et al. |
| 2014/0172013 A1 | 6/2014 | Burbank et al. |
| 2014/0180334 A1 | 6/2014 | Bagaoisan et al. |
| 2014/0194924 A1 | 7/2014 | Tegels et al. |
| 2014/0214075 A1 | 7/2014 | Khosravi et al. |
| 2014/0214076 A1 | 7/2014 | Hundertmark et al. |
| 2014/0236223 A1* | 8/2014 | Porter ............... A61B 17/0401 606/213 |
| 2014/0277111 A1 | 9/2014 | Tegels |
| 2015/0105722 A1 | 4/2015 | Byrne et al. |
| 2015/0342581 A1 | 12/2015 | Mylonakis et al. |
| 2016/0106403 A1 | 4/2016 | Porter et al. |
| 2016/0135796 A1 | 5/2016 | Hundertmark et al. |
| 2016/0345946 A1 | 12/2016 | Yassinzadeh et al. |
| 2017/0135681 A1 | 5/2017 | Akerfeldt |
| 2017/0135682 A1 | 5/2017 | Glazier et al. |
| 2017/0202546 A1 | 7/2017 | Yassinzadeh et al. |
| 2017/0319233 A1 | 11/2017 | Fonger et al. |
| 2018/0008246 A1 | 1/2018 | Bagaoisan et al. |
| 2018/0008247 A1 | 1/2018 | Hundertmark et al. |
| 2018/0070933 A1 | 3/2018 | Walters |
| 2018/0187809 A1 | 7/2018 | Beus et al. |
| 2019/0231326 A1 | 8/2019 | Joe |

FOREIGN PATENT DOCUMENTS

| | | |
|---|---|---|
| EP | 1266626 B1 | 1/2005 |
| EP | 2190356 A1 | 6/2010 |
| EP | 2398392 A1 | 12/2011 |
| EP | 1893100 B1 | 3/2012 |
| EP | 2430982 A2 | 3/2012 |
| EP | 1893099 B1 | 6/2012 |
| EP | 2234654 B1 | 2/2013 |
| EP | 2579788 A1 | 4/2013 |
| EP | 2213247 B1 | 6/2013 |
| EP | 2330981 B1 | 11/2013 |
| EP | 2822629 A1 | 1/2015 |
| EP | 2865319 A1 | 4/2015 |
| EP | 1869301 B1 | 10/2015 |
| EP | 2967525 A1 | 1/2016 |
| EP | 2651310 B1 | 2/2016 |
| EP | 1868510 B1 | 3/2016 |
| EP | 2364112 B1 | 3/2016 |
| EP | 3028648 A1 | 6/2016 |
| EP | 2427121 B1 | 8/2016 |
| EP | 2717782 B1 | 8/2016 |
| EP | 1959888 B1 | 10/2016 |
| EP | 2521493 B1 | 12/2016 |
| EP | 2709535 B1 | 3/2017 |
| EP | 2162071 B1 | 5/2017 |
| EP | 2811912 B1 | 6/2017 |
| EP | 2293724 B1 | 11/2017 |
| EP | 2827938 B1 | 12/2017 |
| EP | 2950722 B1 | 12/2017 |
| EP | 2428167 B1 | 1/2018 |
| EP | 3001954 B1 | 1/2018 |
| EP | 2533698 B1 | 3/2018 |
| EP | 1680029 B1 | 7/2018 |
| KR | 10-2023-0066125 | 5/2023 |
| RU | 29227 U1 | 5/2003 |
| TW | 193270-0001 | 10/2018 |
| TW | 193271-0001 | 10/2018 |
| WO | 2010056915 A1 | 5/2010 |
| WO | 2011161752 A1 | 12/2011 |
| WO | 2012096706 A1 | 7/2012 |
| WO | 20120096706 A1 | 7/2012 |
| WO | 2012148745 A1 | 11/2012 |
| WO | 2014077873 A1 | 5/2014 |
| WO | 2014077878 A1 | 5/2014 |
| WO | 2016077758 A1 | 5/2016 |
| WO | 2017192702 A1 | 11/2017 |
| WO | 2018031539 A1 | 2/2018 |

OTHER PUBLICATIONS

Communication Pursuant to Rule 164(2)(b) and Article 94(3) EPC for European Application No. EP15797812, dated Feb. 1, 2019, 7 pages.

Medline., Hemostasis Valve Obturator [Online], 2019 [Retrieved on Jan. 7, 2019]. Retrieved from the Internet URL: https://www.medline.com/product/Hemostasis-Valve-Obturator/Components-PF62662.

International Preliminary Report on Patentability and Written Opinion for PCT/US2015/060684, dated May 16, 2017, 8 pages.

International Search Report and Written Opinion for Application No. PCT/US2015/060684, dated Apr. 8, 2016, 12 pages.

Office Action dated May 21, 2021, regarding MX/a/2017/006010.

Cordis. Link: https://cordis.com/apac/products/close/endovascular/mynx-control-vascular-closure-device. Visited May 25, 2023, MYNX CONTROL TM Vascular Closure Device (Year: 2023).

YouTube. Link: https://www.youtube.com/watch?v=cgJPmen72rl. Feb. 6, 2023. MYNX CONTROL TM VCD Step by Step Procedure. (Year: 2023).

* cited by examiner

APPARATUS AND METHOD FOR SEALING A VASCULAR PUNCTURE

CROSS REFERENCE TO RELATED APPLICATIONS

The present application is a continuation of U.S. patent application Ser. No. 14/941,222 filed Nov. 13, 2015, which claims priority to U.S. Provisional Patent Application No. 62/079,878 filed Nov. 14, 2014. The entire disclosure contents of these applications are herewith incorporated by reference into the present application.

FIELD

Percutaneous apparatuses and methods for sealing a vascular puncture using a plug or sealant.

BACKGROUND

To obtain percutaneous access to a patient's vasculature, a hollow needle may be inserted through a patient's skin and into a blood vessel. A guide wire may be passed through the needle lumen into the blood vessel, whereupon the needle may be removed. An introducer sheath may then be advanced over the guide wire into the vessel in conjunction with or subsequent to one or more dilators. A catheter or other device may be advanced through the introducer sheath and over the guide wire into a position for performing a medical procedure. Upon completing the procedure, the device(s) and introducer sheath may be removed, leaving a puncture extending between the skin and the vessel wall. To seal the puncture, external pressure may be applied to the overlying tissue, e.g., manually and/or using sandbags, until hemostasis occurs.

After completion of a diagnostic or therapeutic procedure requiring access to the vasculature (e.g., imaging procedure, angioplasty, stent delivery, or otherwise), the arteriotomy can be closed by various mechanical or biological solutions, such as by applying external pressure, cinching, suturing, and/or delivering metal implants, plugs, or sealants. However, many of these closure procedures may be time consuming, expensive, and uncomfortable for the patient, requiring the patient to remain immobilized in the operating room, catheter lab, or holding area for long periods of time. Additionally, some of these prolonged closure procedures may increase the risk of hematoma from bleeding prior to hemostasis.

Some closure procedures may require a sheath exchange between the introducer sheath used during the diagnostic or therapeutic procedure and a sheath that is compatible with the closure system. This additional step may be time consuming and increases the risk of vessel injury and infection. Accordingly, there is still a need for a closure method that eliminates the sheath exchange step. The present disclosure is directed toward a closure system that is compatible with a standard procedural sheath and integrates the standard procedural sheath into a sealant delivery method.

SUMMARY

Certain aspects of the disclosure are directed toward methods and closure systems for sealing an arteriotomy. The closure system can be introduced through a standard procedural sheath and can include a sheath adapter configured to engage the procedural sheath, particularly a side port or an irrigation line of the procedural sheath.

Introducing the closure system through the existing procedural sheath eliminates the need for a custom sheath as well as eliminating the steps associated with a sheath exchange, including insertion of a guidewire, removing the existing sheath and inserting the custom sheath. Elimination of sheath exchange reduces risk of arterial trauma and vessel damage, maintains arterial access, saves time, limits leakage and bleeding and minimizes the possibility of hematoma or infection. In order to eliminate the need for a custom sheath, an integrated sheath can be provided within the closure system and can be comprised of two sleeves, an inner and an outer sleeve.

In certain aspects, the method can include advancing a closure system through a procedural sheath extending through the arteriotomy. The method can also include securing the sheath adapter of the closure system to the procedural sheath by releasably attaching the attachment structure of the sheath adapter to a side port or an irrigation line of the procedural sheath, and retracting the handle portion to retract the procedural sheath and the outer catheter relative to the inner catheter to expose the sealant. The method can further include tamping the sealant with the support tube member.

In certain aspects, the closure system can include a handle portion, and a sheath adapter extending from the handle portion. The sheath adapter can include an attachment structure for releasable attachment to a procedural sheath.

In certain aspects, the closure system can include an outer catheter extending from a handle portion. The outer catheter can include a proximal section and a distal section. The distal section can include an inner sleeve and an outer sleeve surrounding the inner sleeve. The inner sleeve can include a first slit, and the outer sleeve can include a second slit circumferentially displaced from the first slit. The slit in the outer sleeve or primary sleeve can be provided to mitigate jamming of the sleeve/sealant and to ease friction as the sleeve is retracted during sealant delivery. The inner sleeve or secondary sleeve can be provided to help contain the sealant when the tip of the catheter is introduced into the vessel.

Optionally, any of the closure systems described above can include an inner catheter extending through an outer catheter, a support tube radially between the outer catheter and the inner catheter, and/or a sealant positioned in a distal section of the outer catheter.

In certain aspects, the closure system can include a first actuator configured to unlock the inner catheter with respect to the handle. The handle can include a second actuator configured to advance a support tube or member through the procedural sheath to help tamp the deployed sealant. For example, the handle can include a cam drive mechanism, the cam can be linked to the second actuator and configured to cause the support member to move. In certain aspects, the handle can further include a third actuator configured to retract the expandable structure through the sealant. The third actuator can be a retraction slider that moves relative to the inner housing portion.

In an alternative embodiment, the closure system can comprise a first actuator that is configured to both retract the outer sleeve, thus at least partially exposing the sealant, and to tamp the sealant against the arteriotomy. A second actuator can be provided to retract the expandable structure.

A closure system that comprises a handle that has at least one actuator or other type of controller mechanism that can reveal the sealant, tamp the sealant and/or retract the expandable structure is provided herein. In another embodiment, a closure system that comprises a handle having at least two actuators or any other type of controller mechanism that can reveal the sealant, tamp the sealant and retract the expandable structure, alone or in any combination thereof. In yet another embodiment, a closure system is provided that comprises a handle having at least three actuators or any other type of controller mechanism that can reveal the sealant, then tamp the sealant and finally retract the expandable structure.

Any feature, structure, or step disclosed herein can be replaced with or combined with any other feature, structure, or step disclosed herein, or omitted. Further, for purposes of summarizing the disclosure, certain aspects, advantages, and features of the devices have been described herein. It is to be understood that not necessarily any or all such advantages are achieved in accordance with any particular embodiments disclosed herein. No individual aspects of this disclosure are essential or indispensable.

BRIEF DESCRIPTION OF THE DRAWINGS

FIGS. 1A-1I illustrate a method of using an embodiment of a closure system for delivering a sealant to an arteriotomy site.

Figure 1A:
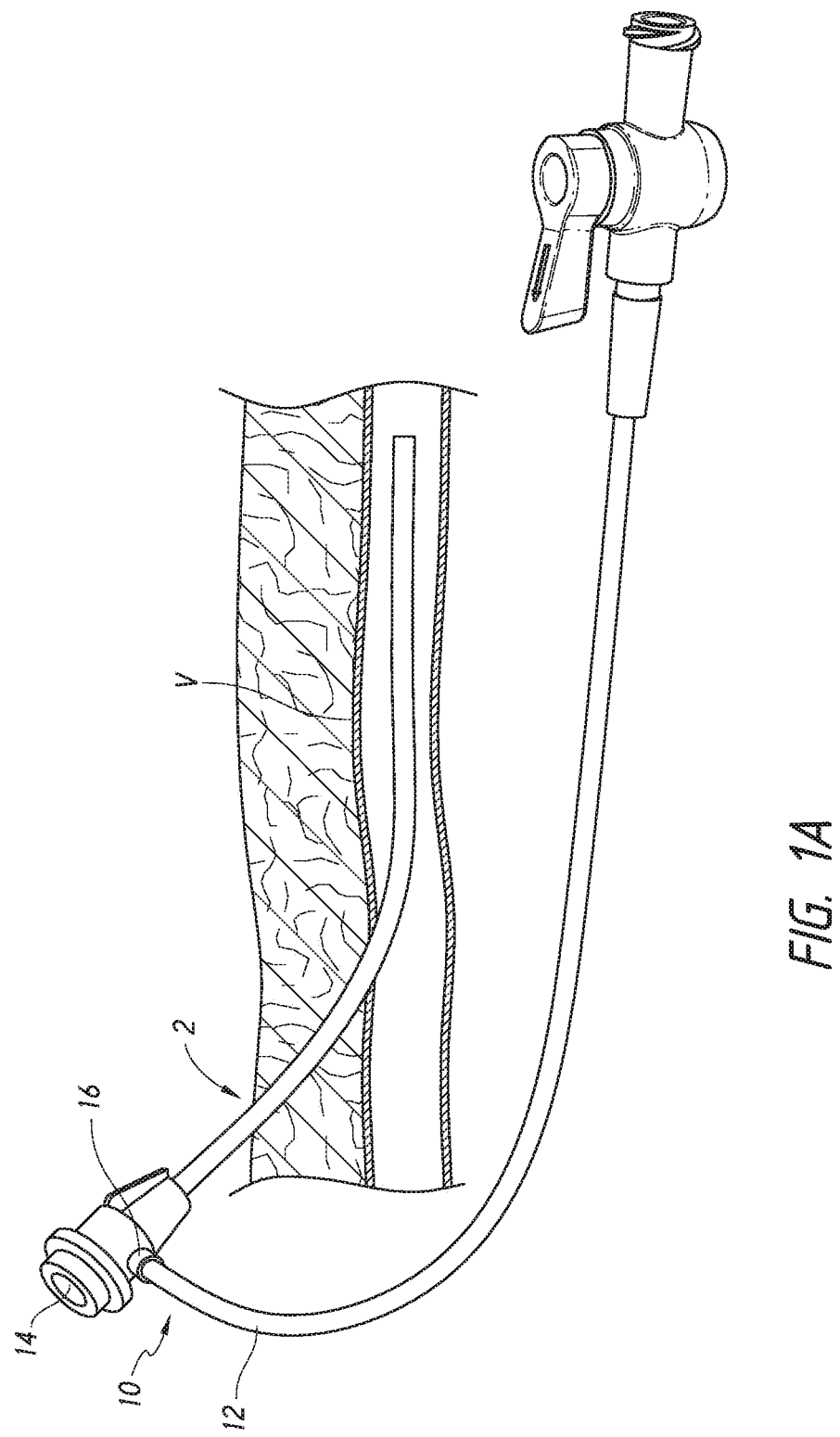

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

A closure system for delivering a sealant to an arteriotomy and a method of use for sealing same is provided herein. The closure system further includes a sheath adaptor for attachment to an existing procedural sheath and, thus, avoiding the need for a sheath exchange by removing the procedural sheath and inserting another sheath. FIGS. 1A-1I illustrate a method of delivering a sealant 18 to an arteriotomy site 2 using a closure system 20. In general, the closure system 20 can include a handle portion 30 having a first actuator 32, a second actuator 34, and a third actuator 36 that can be used to control the features of the closure system 20. An outer catheter 22 can extend from the handle portion 30 and can move axially with the handle portion 30. The handle portion 30 can include a sheath catch 40, or sheath adaptor, at a distal section of the handle portion 30.

An inner catheter 24 can extend through the outer catheter 22. The inner catheter 24 can include an expandable structure 26 positioned at a distal section of the inner catheter 24. The inner catheter 24 can move axially relative to the outer catheter 22, for example, by actuating the first actuator 32 to release the inner catheter 24 from the outer catheter 22 and by retracting or advancing the third actuator 36 to move the inner catheter 24. Although the examples provided herein will describe the expandable structure 26 as a balloon, the expandable structure could alternatively be a basket, expandable wire braid, expandable mesh, expandable frame, rotatable structure, and the like. In an alternative embodiment, the expandable structure may include a bioabsorbable foot plate or other element on one end, e.g., for providing tactile feedback to the user during a sealing procedure and/or sealing the puncture.

The sealant 18 can be positioned in a distal section 60 of the outer catheter 22, radially between the inner catheter 24 and the outer catheter 22. For example, the inner catheter 24 can extend through the sealant 18, while the outer catheter 22 surrounds the sealant 18. The sealant 18 may include a first, proximal or main section formed from freeze-dried hydrogel, and a second, distal, or tip section (not shown) formed from a plurality of non-freeze-dried and/or non-cross-linked precursors, e.g., formed as a solid mass or solid plug, fused or otherwise attached to and extending distally from the first section, as disclosed in U.S. application Ser. No. 13/354,278, titled "Apparatus and Methods for Sealing a Vascular Puncture," filed Jan. 19, 2012, and incorporated herein by reference in its entirety. Additional details regarding sealant composition can be found in U.S. Pat. No. 7,335,330, titled "Apparatus and methods for sealing a vascular puncture," filed Nov. 5, 2004, and incorporated herein by reference in its entirety.

A support tube 28 or support member can be positioned proximal to the sealant 18, radially between the inner catheter 24 and the outer catheter 22. For example, the support member 28 can be tubular such that the inner catheter 24 can extend through the support member 28, while the outer catheter 22 surrounds the support member 28. Thus, the support member 28 can include a lumen extending between a proximal end and distal end to accommodate slidably receiving the inner catheter 24 therethrough. The support member 28 can support the sealant 18 during the positioning of the sealant 18 and tamp the sealant 18 against the vessel wall V to close the arteriotomy 2. The support member 28 may be substantially rigid, semi-rigid, and/or substantially flexible, e.g., having sufficient column strength to allow proximal movement of the closure system relative to the sealant 18 without buckling the support member 28 and/or to allow the distal end of the support member 28 to be advanced to compress the sealant 18 within a puncture. The support member 28 can move axially relative to the outer catheter 22 and the expandable structure on the inner catheter 24, for example, by actuating the second actuator 34. In some configurations, actuating the second actuator 34 can release the inner catheter 24 from the support member 28.

In combination with or in place of any of the features described herein, the closure system 20 can include any of the features of the sealant delivery apparatuses described in U.S. Publication No. 2014/0025103, filed Sep. 25, 2013, which is hereby incorporated by reference in its entirety.

FIG. 1A illustrates a procedural sheath 10 extending through an arteriotomy 2. The procedural sheath 10 can be the same sheath used during the diagnostic and/or therapeutic procedure. As shown in FIG. 1A, the procedural sheath 10 can include a hub portion 14 having a side port 16. The side port 16 can be secured to an irrigation and/or aspiration line 12.

Figure 1B:
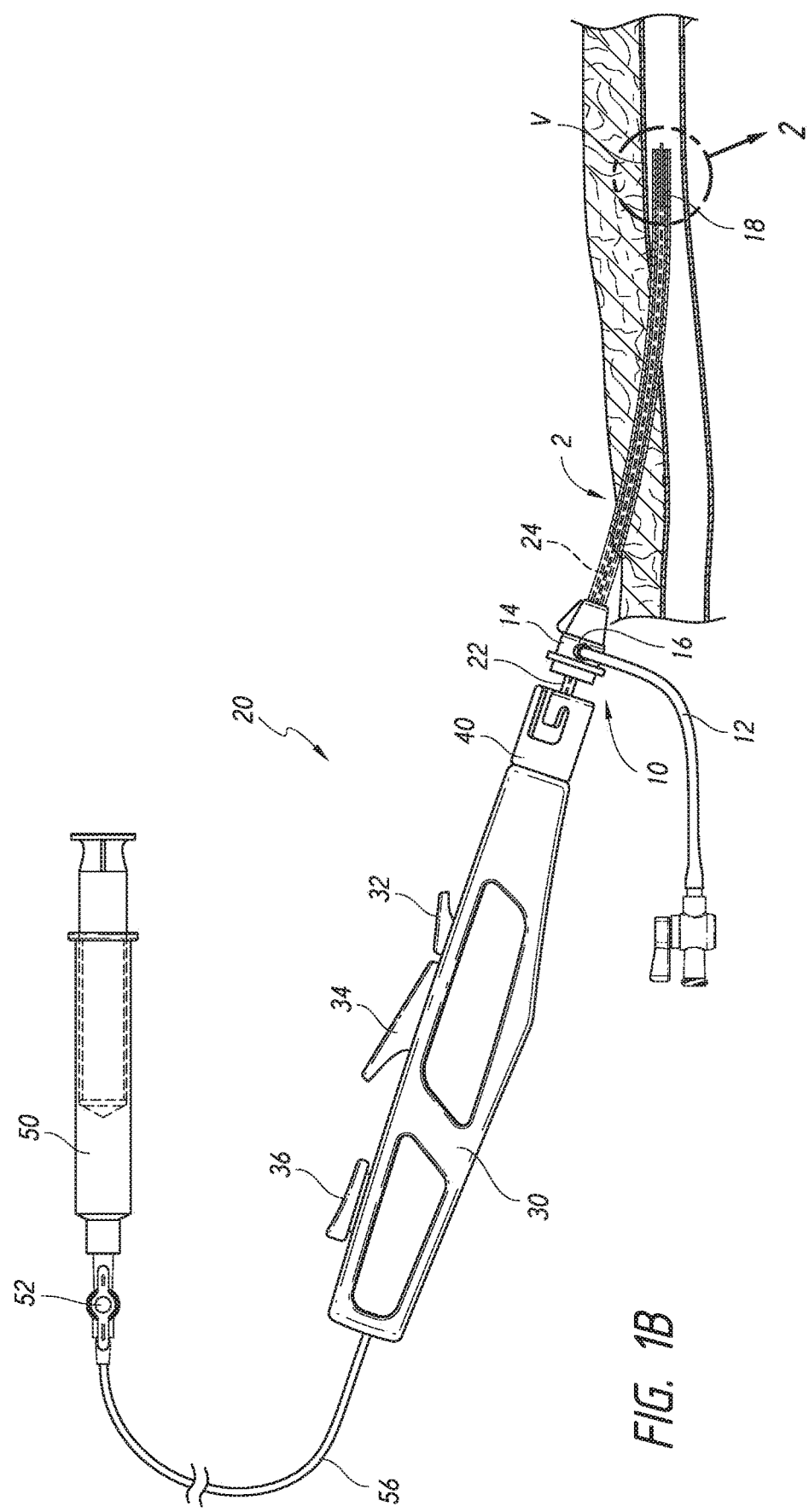

After the diagnostic and/or therapeutic procedure, the closure system 20 can be introduced through the procedural sheath 10 by introducing the outer catheter 22 through the hub portion 14 (see FIG. 1B). The outer catheter 22 can be sized to be compatible with 5 F or larger standard procedural sheaths.

Figure 1C:
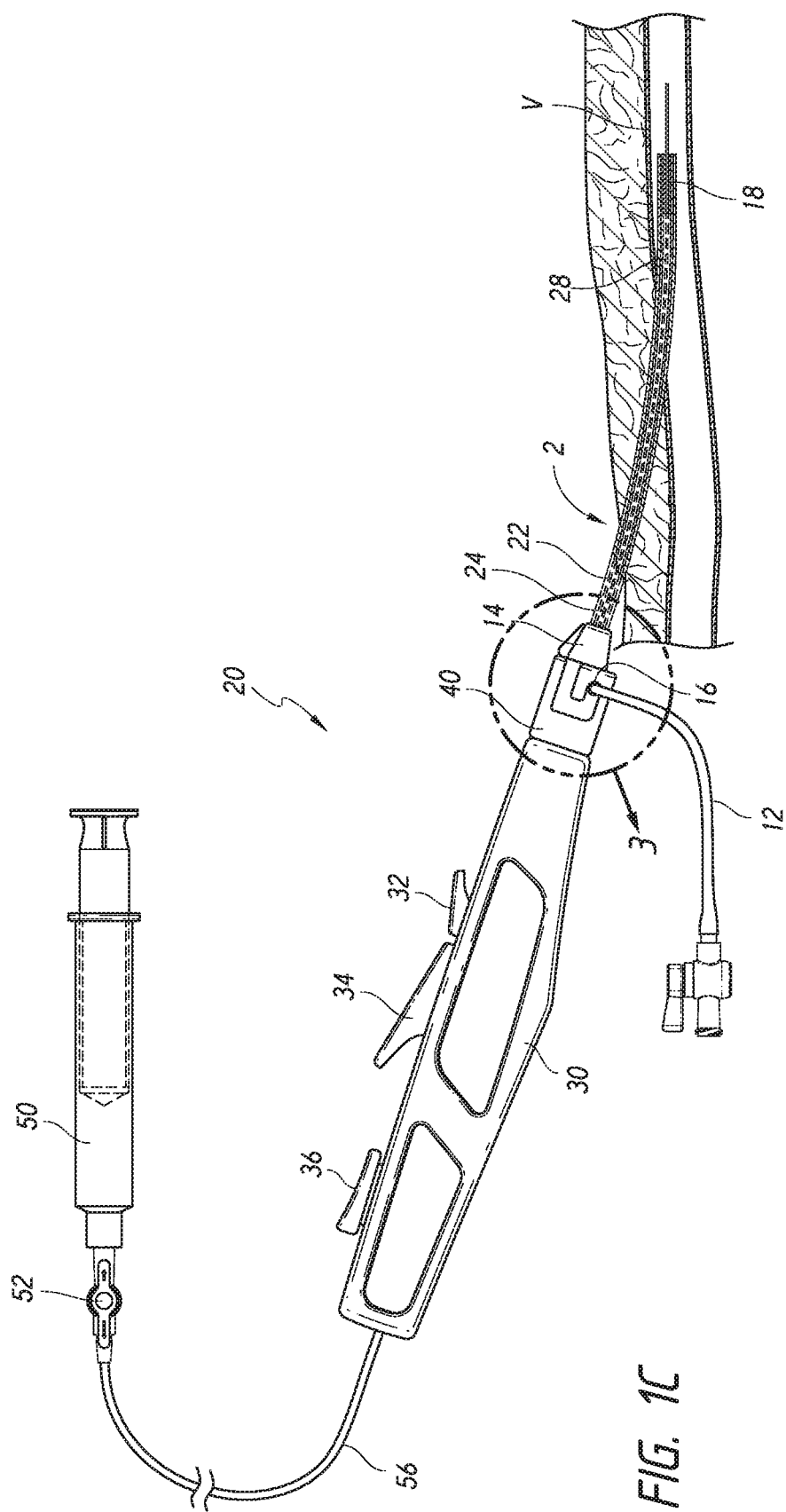

The closure system 20 can be advanced through the procedural sheath 10 until the sheath adaptor 40 engages the hub portion 14 of the procedural sheath 10 (see FIG. 1C). As described in further detail below, the sheath adaptor 40 can be designed to removably engage the side port 16 or irrigation line 12 of the hub portion 14.

Figure 1D:
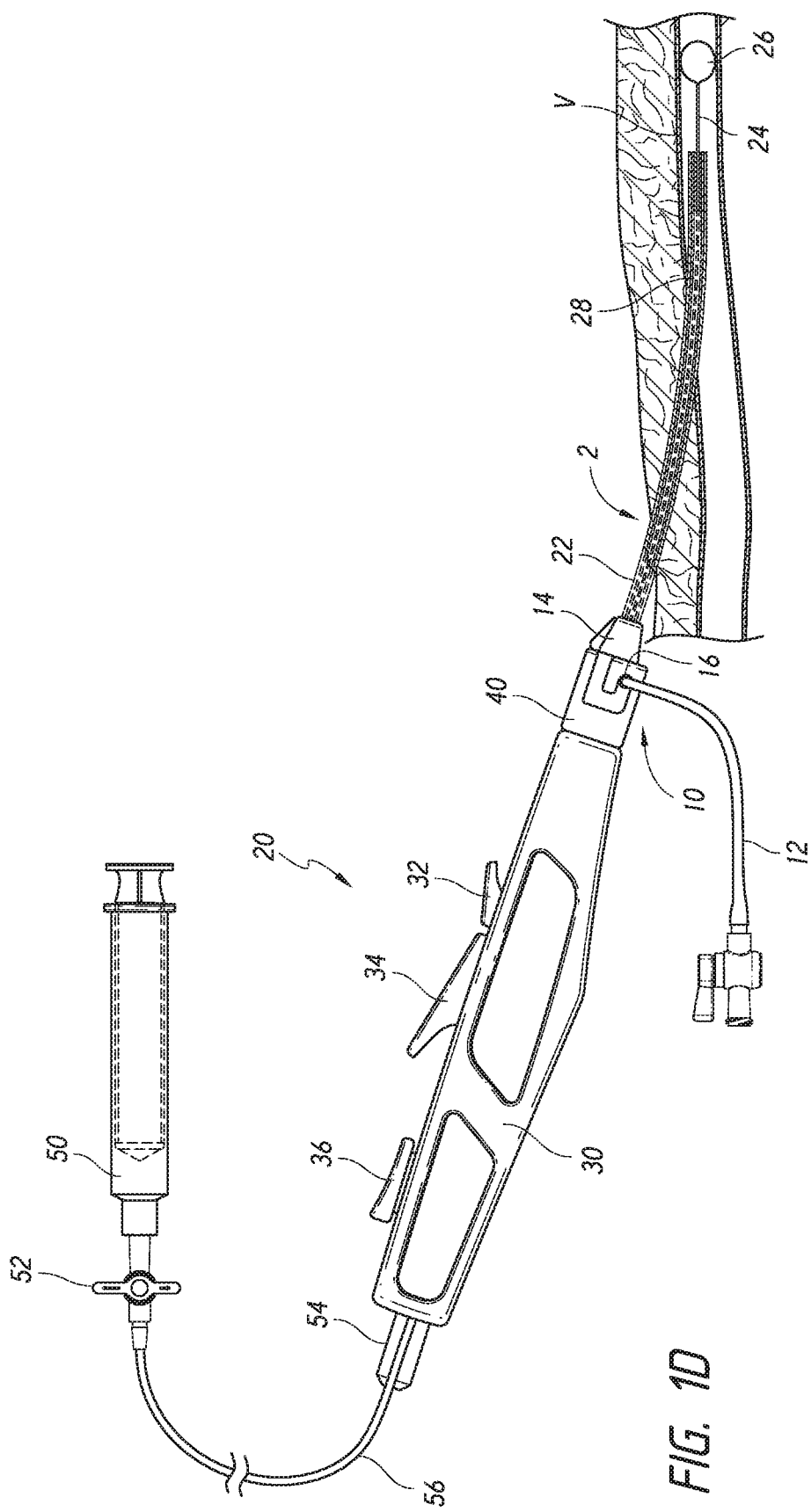

With the closure system 20 coupled to the procedural sheath 10, the expandable structure 26 of the inner catheter 24 can be expanded using the syringe 50 (see FIG. 1D). The expandable structure 26 can be expanded until the inflation indicator 54 indicates the expandable structure 26 has been expanded to a pre-determined pressure. For example, the inflation indicator 54 can move from a first position to a second position when the expandable structure 26 is fully expanded. As shown in FIG. 1D, the inflation indicator 54 in the second position can protrude from a proximal end of the handle portion 30; however, the inflation indicator 54 can be positioned elsewhere on the handle portion 30. Alternatively, any other appropriate inflation indicator can be employed. One alternative can include a pressure gauge with a dial that has a needle indicator that displays pressure readings and can show the complete inflation of the balloon. After the expandable structure 26 has been expanded, the inflation line 56 can be sealed by closing the valve 52.

Figure 1E:
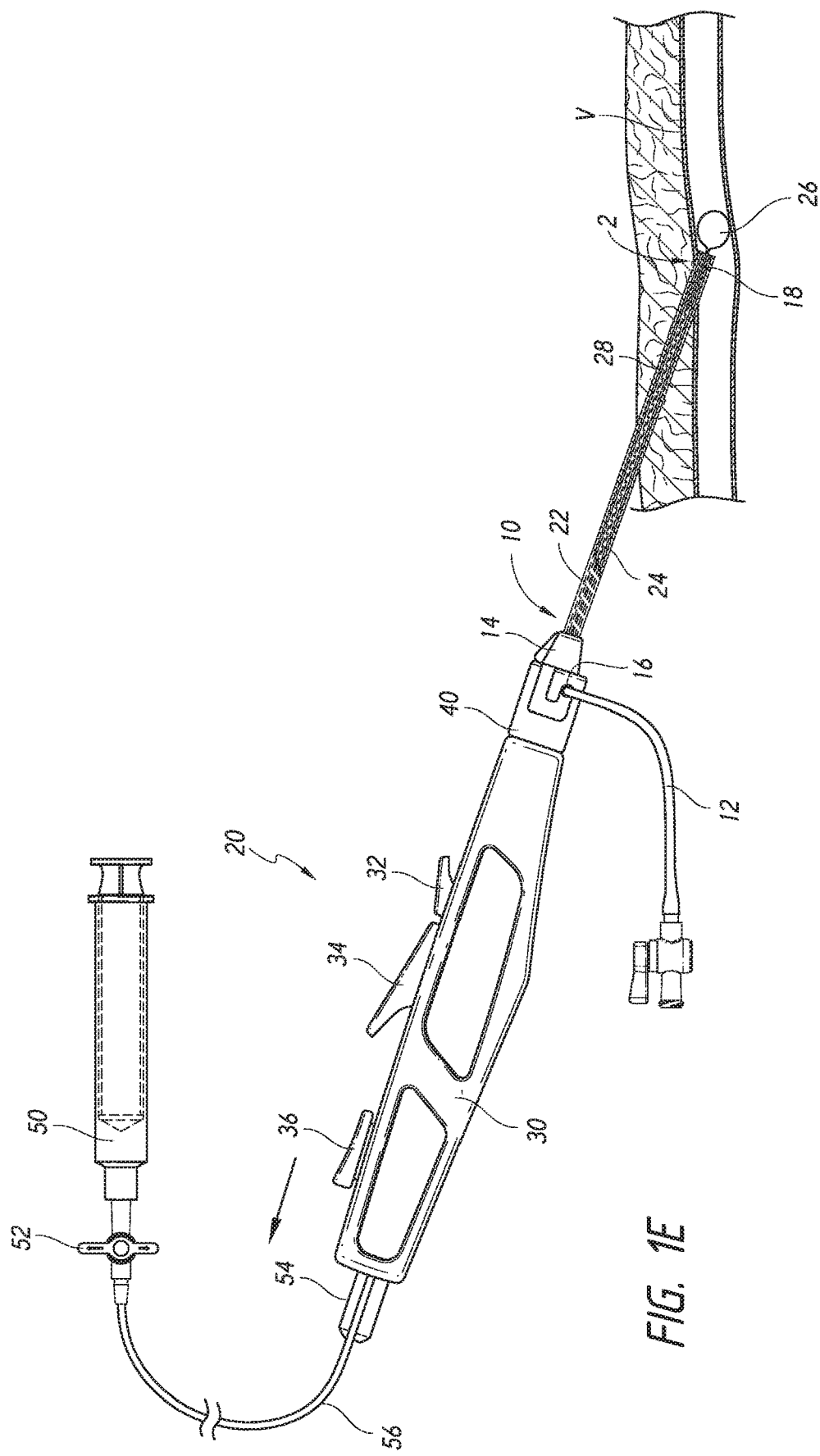
Figure 1F:
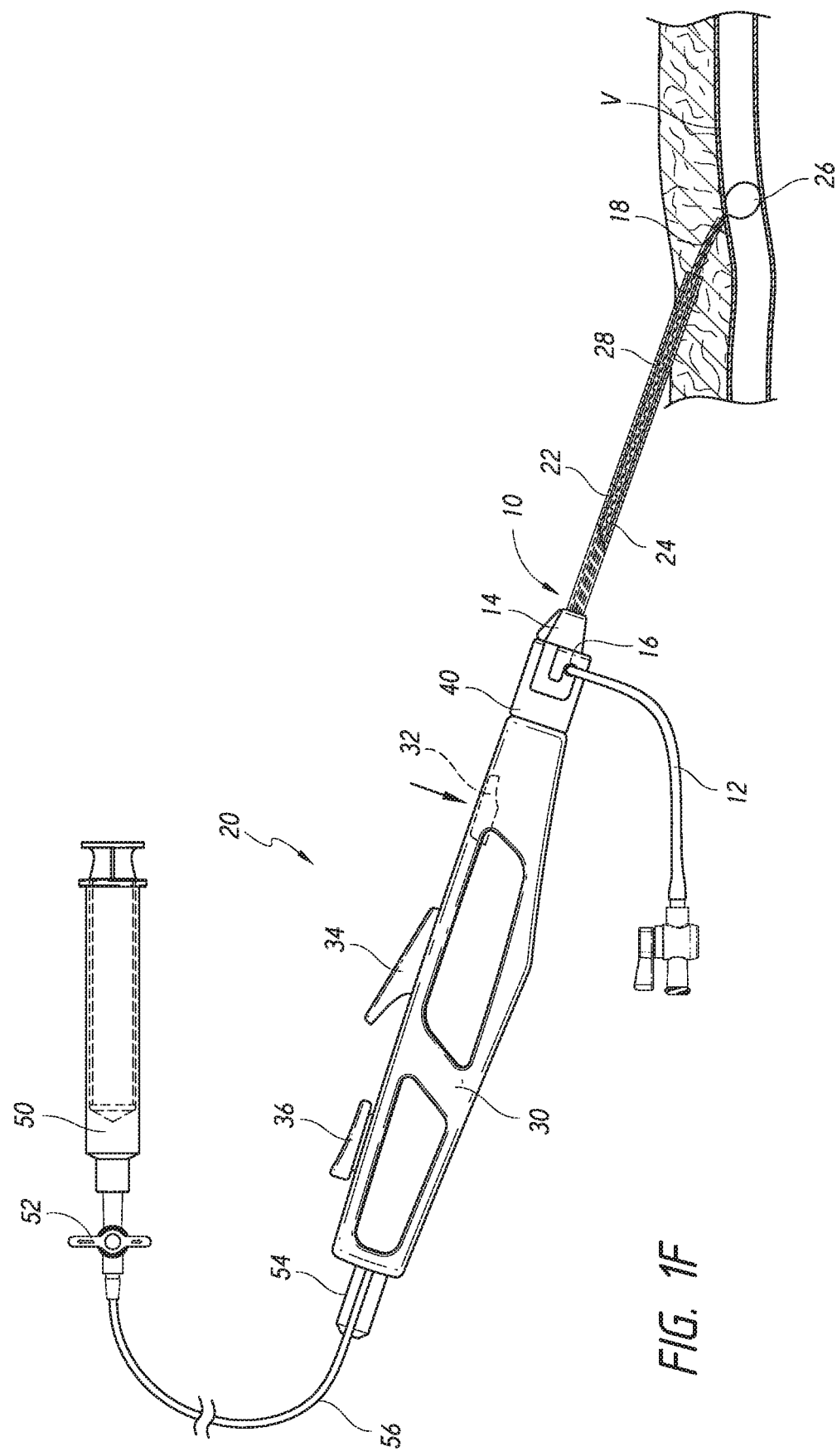
Figure 1G:
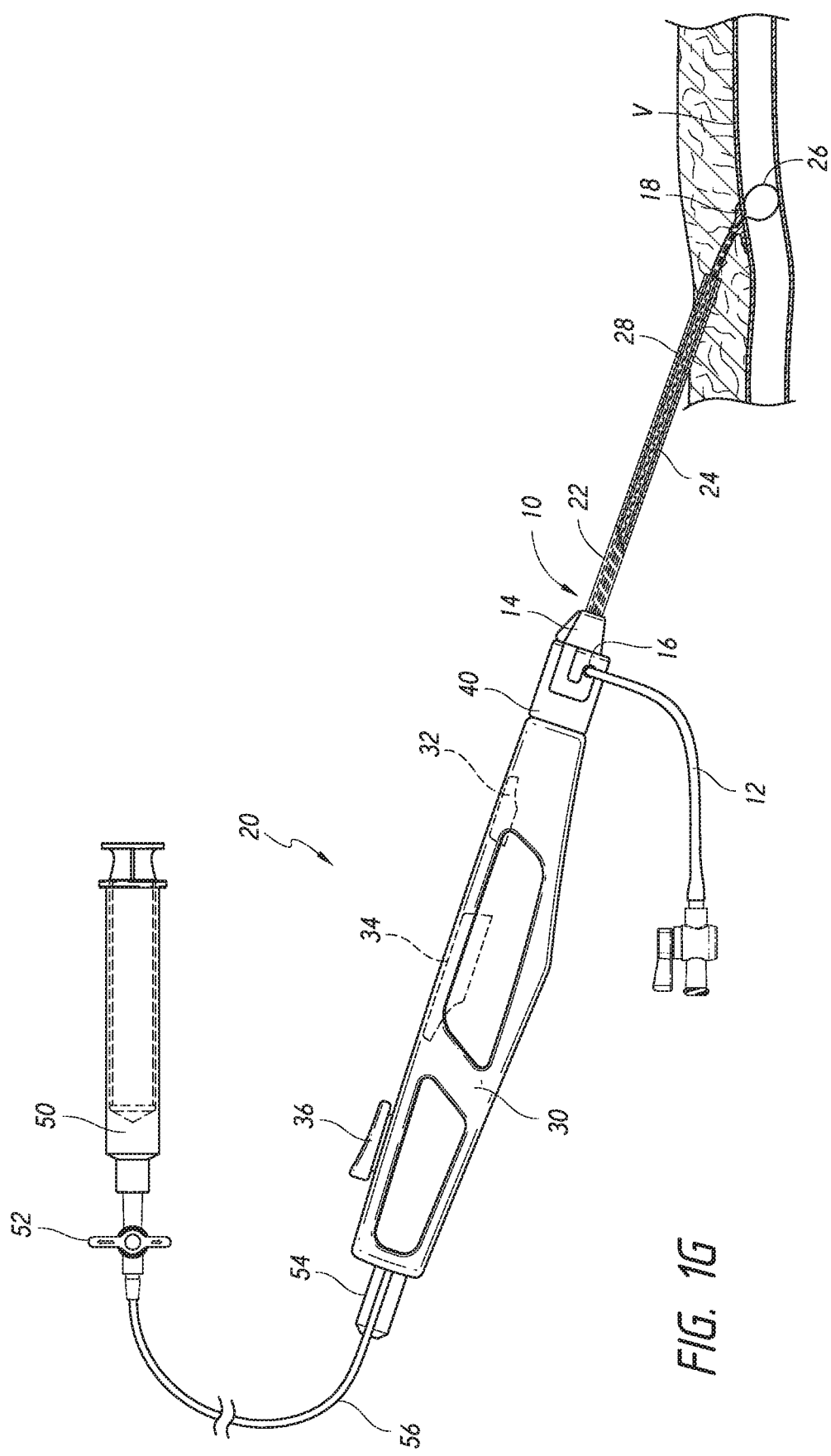

With the expandable structure 26 expanded, the closure system 20 and the procedural sheath 10 can be retracted until the expandable structure 26 abuts an inner surface of the vessel wall V (see FIG. 1E).

The inner catheter 24 can be released from the outer catheter 22 by actuating or depressing the first actuator 32. After the inner catheter 24 has been released, the procedural sheath 10 and the outer catheter 22 can be retracted relative to the inner catheter 24 to expose the sealant 18 (see FIG. 1F). In this configuration, the handle portion 30 can slide over the first actuator 32 to retract the outer catheter 22, while the inner catheter 24 remains in place.

With the sealant 18 exposed, the support member 28 can be advanced to tamp the sealant 18 against an outer surface of the vessel wall V. As described above, actuation or depression of the second actuator 34 can advance the support member 28 relative to the inner catheter 24 and the outer catheter 22.

Figure 1H:
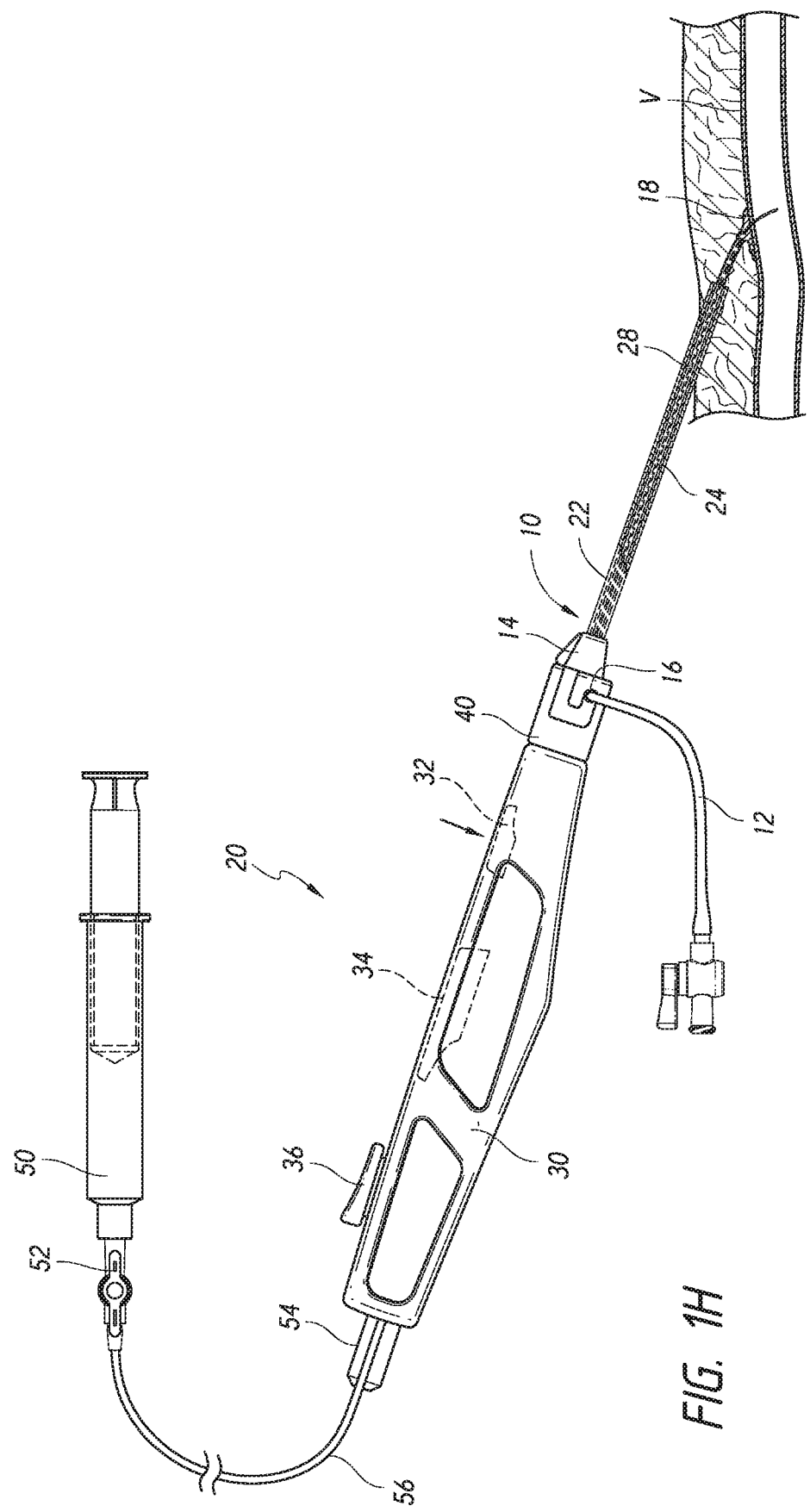
Figure 11:
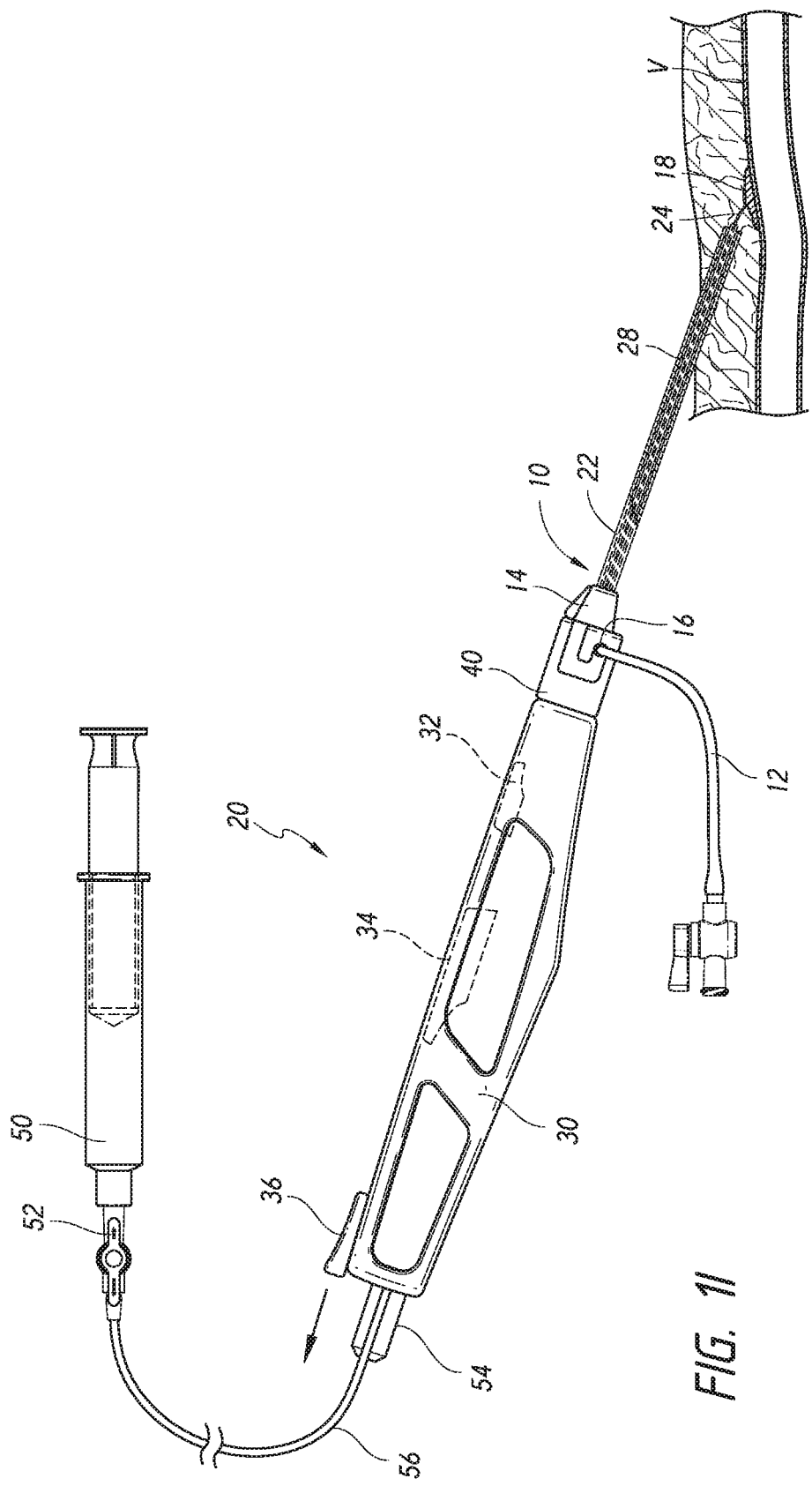
FIGS. 11A-C illustrate one aspect of a visual indication system on the handle shown in FIGS. 9A-9G.

After the sealant 18 has been tamped, the expandable structure 26 can be contracted, for example, by opening the valve 52 and deflating the expandable structure 26 using the syringe 50 (see FIG. 1H). With the expandable structure 26 contracted, the expandable structure 26 can be retracted through the sealant 18 by actuating or depressing the third actuator 36. The inner catheter 24 can be retracted relative to the outer catheter 22 and/or support member 28 (see FIG. 1I). After the expandable structure 26 has been retracted through the sealant 18, the entire closure system 20 and procedural sheath 10 can be removed from the body, leaving the sealant 18 in place against the vessel wall V. Since the sheath adapter 40 is coupled to the procedural sheath 10, the closure system 20 and the procedural sheath 10 can be removed together, but the closure system 20 could be disengaged from the procedural sheath 10 and removed separately.

Figure 2:
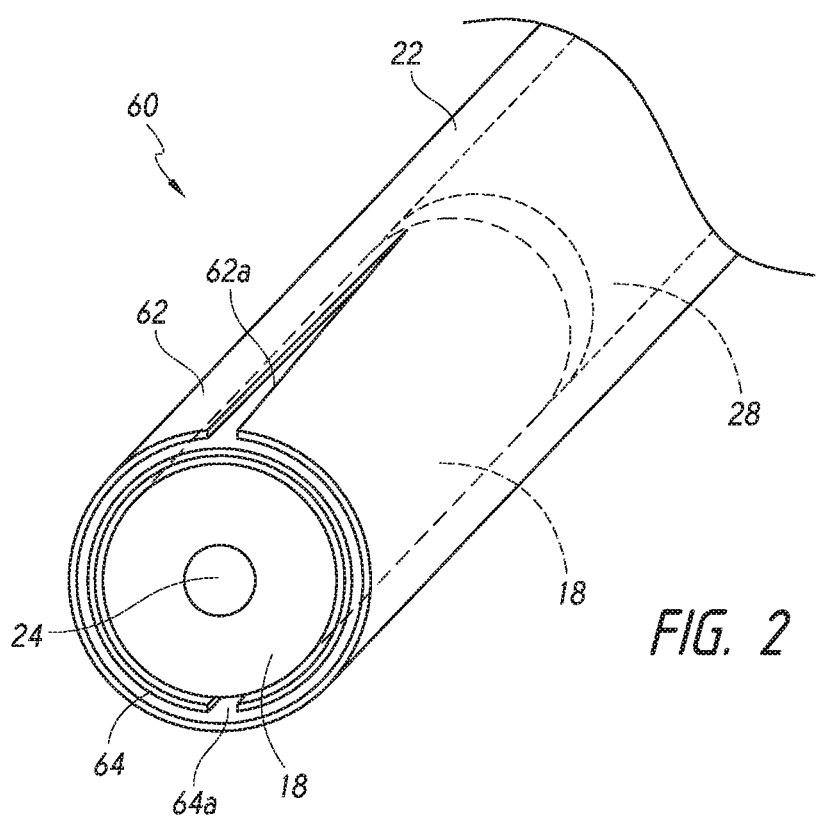
FIG. 2 illustrates an enlarged view of a distal portion of the closure system shown in FIG. 1B taken through line 2-2.

FIG. 2 illustrates an enlarged view of the closure system 20 prior to sealant delivery. As described above, the sealant 18 can be positioned in a distal section 60 of the outer catheter 22, radially between the inner catheter 24 and the outer catheter 22. The support member 28 can be positioned proximal to the sealant 18. At least the distal section 60 of the outer catheter 22 can include an outer sleeve 62 and an inner sleeve 64. Each of the outer sleeve 62 and the inner sleeve 64 can include at least one slit 62a, 64a, respectively (e.g., one slit, two slits, three slits, or more). The outer sleeve 62 and the inner sleeve 64 can include the same number of slits or different numbers of slits. The slits 62a, 64a can be positioned so that the slits are not aligned with each other. In one aspect, the outer slit 62a can be positioned opposite the inner slit 64a (e.g., about 180 degrees apart). The inner and outer sleeves 62, 64 can be overlapping such that the sealant 18 is circumferentially surrounded by the combination of the inner and outer sleeves 62, 64 to minimize exposure to bodily fluids entering the outer catheter 22 through the slits 62a, 64a.

In one aspect, the outer sleeve 62 can be longer than the inner sleeve 64. The outer sleeve 62 can extend back to the handle portion 30, for example such that it is integral with the outer catheter, while the inner sleeve 64 can be secured to the outer sleeve 62 proximal to the slits 62a, 64a. The inner sleeve 64 and the outer sleeve 62 can be attached using a thermal attachment, adhesive bond, mechanical bond, or other appropriate attachment method. With the inner sleeve 64 disposed within the outer sleeve 62, an inner diameter of the distal section 60 can be less than an inner diameter of a proximal section of the outer catheter 22.

In one instance, the inner sleeve 64 can be stiffer than the outer sleeve 62 to provide support for the outer sleeve 62. For example, the inner sleeve 64 and the outer sleeve 62 can have varying thicknesses and/or be constructed from different materials. In one embodiment, the inner sleeve 64 can be constructed from polyimide or a similarly rigid polymer, while the outer sleeve 62 can be constructed from a softer material, such as polyamide. In another embodiment, the outer sleeve 62 can be constructed from a polyether block amide, such as Pebax®, or from a nylon material. However, any other appropriate materials may be used for the inner and outer sleeves. Although not shown, in another aspect, the outer sleeve 62 can be thermally shaped with a smaller radius at the distal end to provide an atraumatic tip during delivery.

The dual layer sleeve 62, 64 can help maintain the sealant in the closure system 20 when the closure system 20 is being retracted through the arteriotomy. The slit design of the distal section 60 reduces friction during deployment of the sealant and reduces the risk of jamming the sealant. For example, if the sealant 18 begins to expand while still positioned in the closure system 20 (e.g., from bodily fluids entering from a distal end), the slit design of the distal section 60 provides space for the sealant 18 to expand without jamming the closure system 20.

FIGS. 9A-9G illustrate a second embodiment of a closure system 120. In this embodiment, the closure system 120 can comprise one or more actuators that assist in deploying the sealant, tamping the sealant and retracting the expandable structure and, in particular, three actuators. Similar features to the first embodiment illustrated and discussed in FIGS. 1A-1I have similar numbers.

Figure 9A:
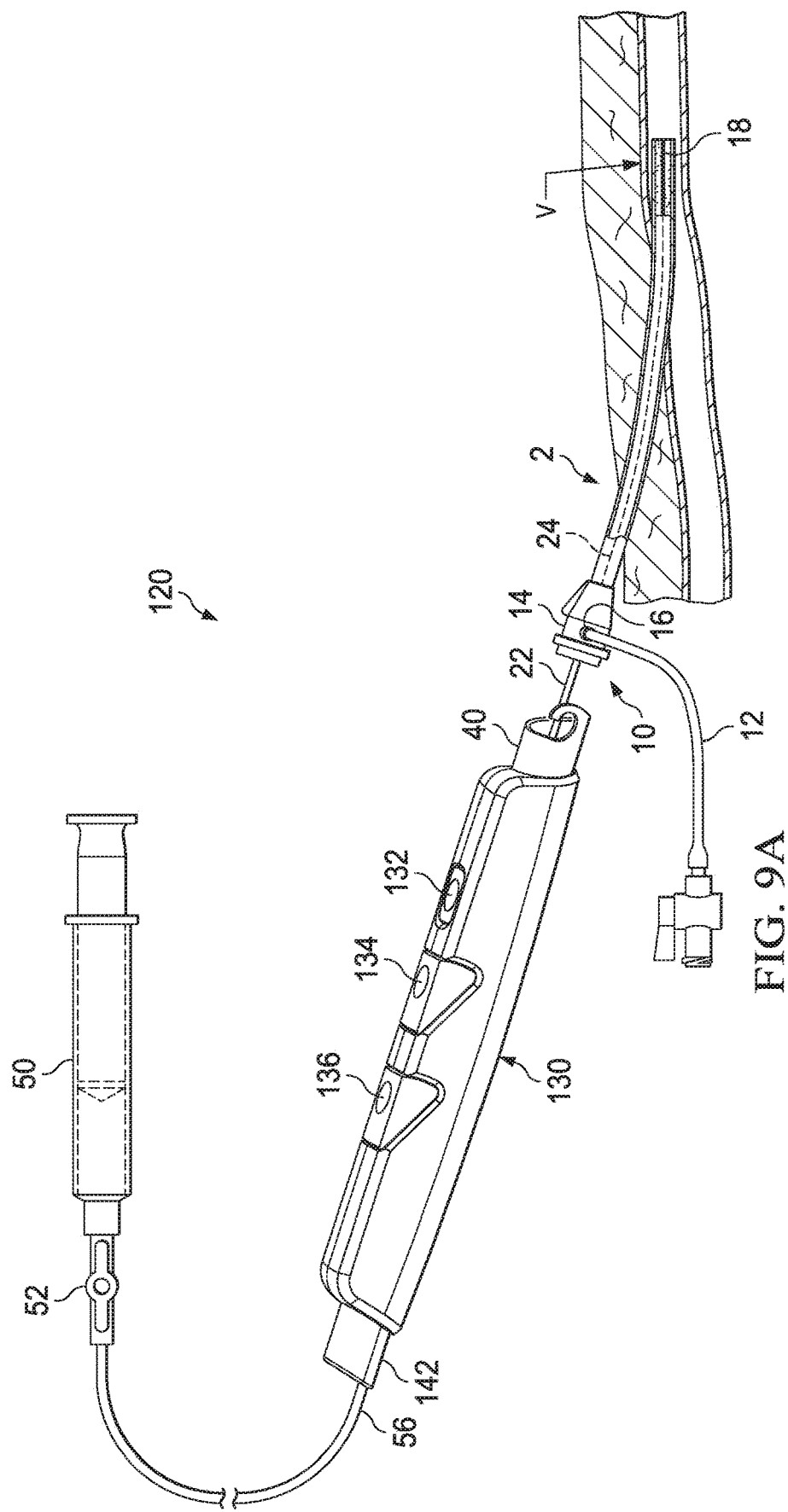
FIGS. 9A-9G illustrate a method of using a second embodiment of a closure system for delivering a sealant to an arteriotomy site.

Similar to the function of the closure system 20 in FIG. 1B, the closure system 120 can be introduced through the procedural sheath 10 by introducing the outer catheter 22 through the hub portion 14 (see FIG. 9A). The outer catheter 22 can be sized to be compatible with 5 F or larger standard procedural sheaths.

The closure system 120 can be advanced through the procedural sheath 10 until the sheath adaptor 40 engages the hub portion 14 of the procedural sheath 10. As described in further detail below, the sheath adaptor 40 can be designed to removably engage the side port 16 or irrigation line 12 of the hub portion 14.

Similar to the first embodiment presented above, the inner catheter 24 can extend through the outer catheter 22. The inner catheter 24 can include an expandable structure 26, such as a balloon or other appropriate element as discussed above, positioned at a distal section of the inner catheter 24. The inner catheter 24 can move axially relative to the outer catheter 22, for example, by actuating or depressing the first actuator 32 to release the inner catheter 24 from the outer catheter 22 and by actuating or depressing the third actuator 36 to move the inner catheter 24 into the support member 28. In order to provide compatibility with the existing procedural sheath, the sheath of the closure system is integrated with the device handle. This can be accomplished by providing the inner sleeve 64 and the outer sleeve 62 which form the inner/outer sleeve assembly, e.g., the two sleeves at the distal end. This integrated sheath, e.g., outer catheter 22, can be fixed to the handle and retracts during sealant deployment. The outer catheter 22 can move radially within the handle to minimize the impact of torsional forces on the outer catheter 22 and on the outer sleeve 62; this can allow the outer sleeve 62/catheter 22 to rotate freely within the handle.

Figure 9B:
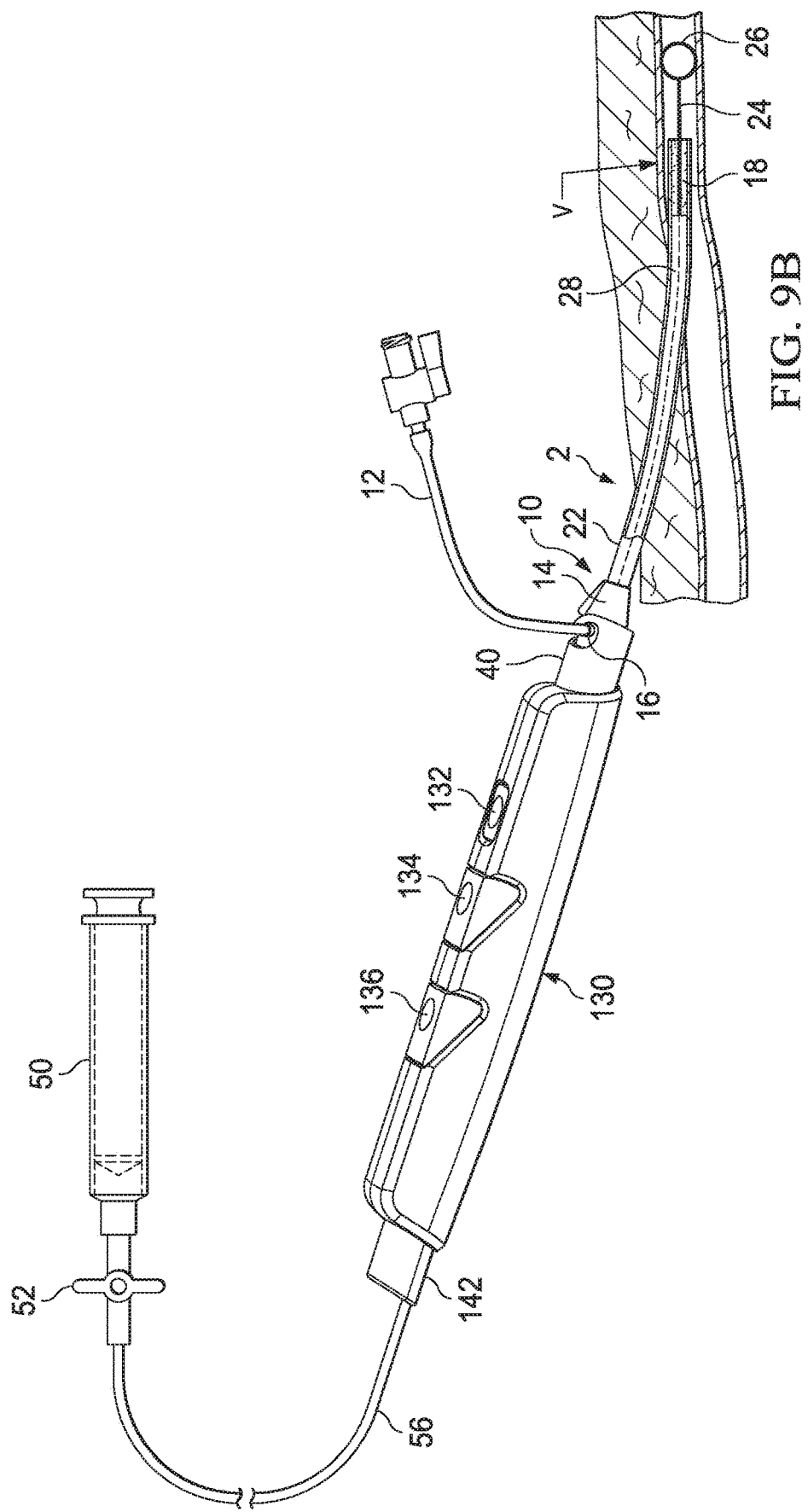
Figure 9C:
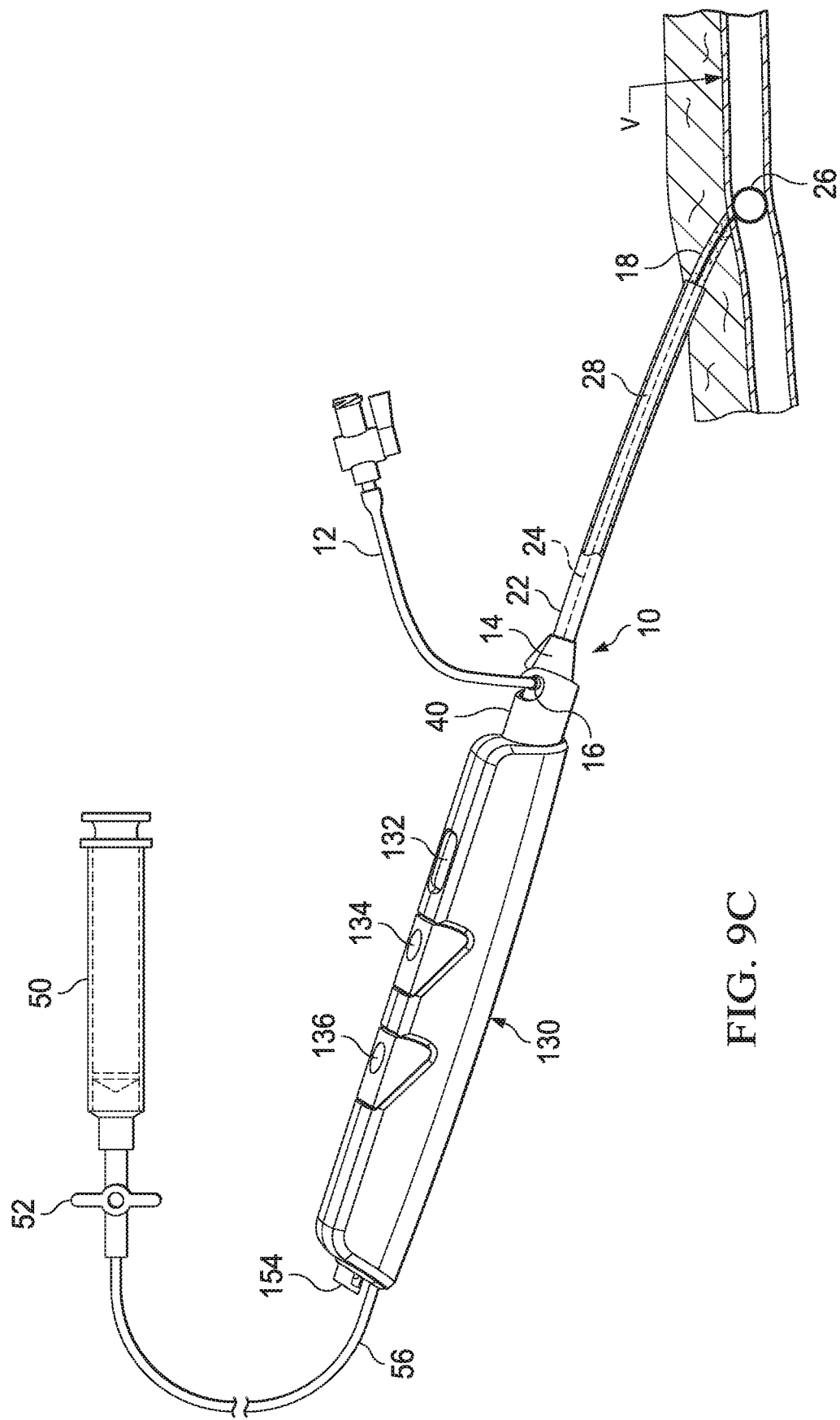
Figure 9D:
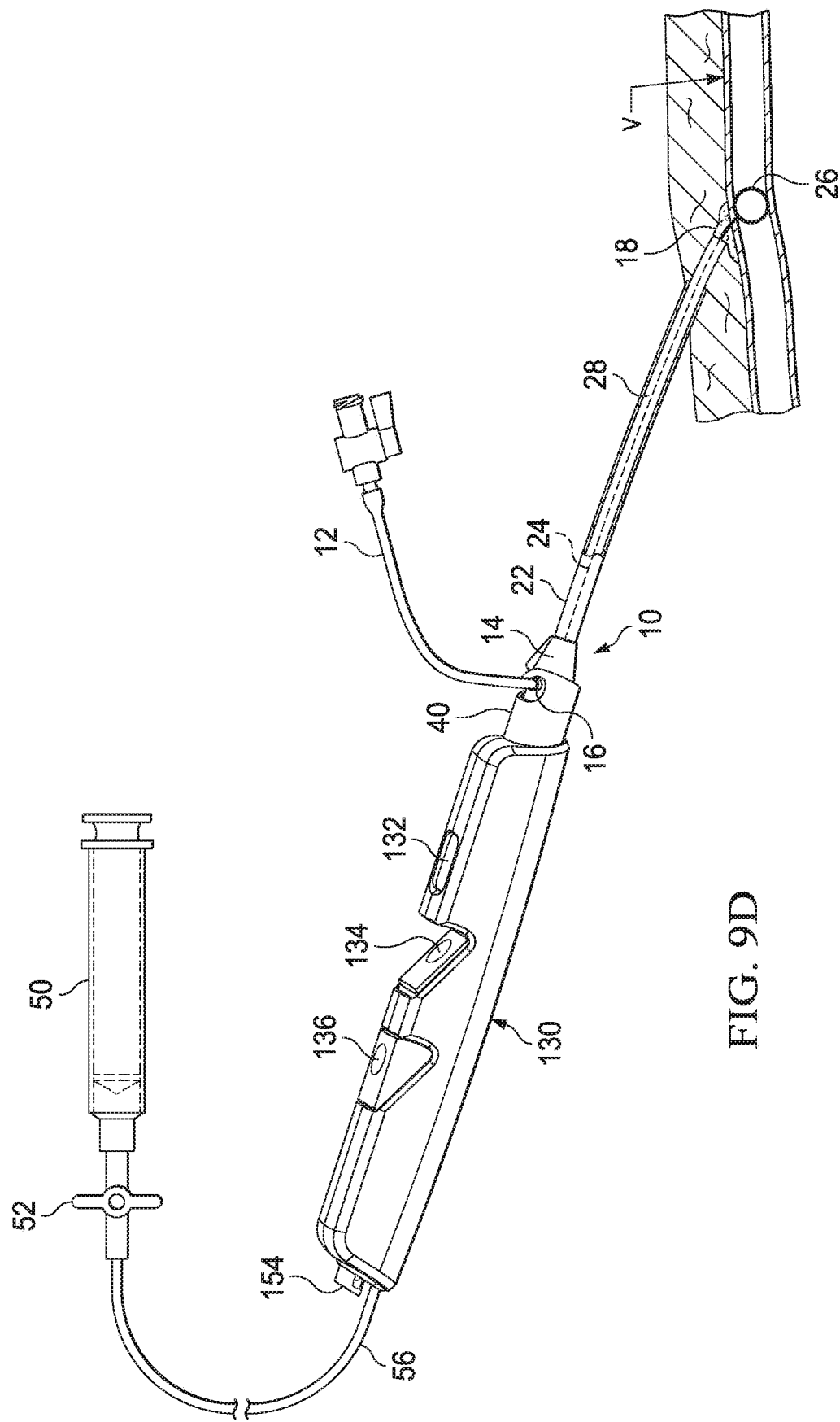

With the closure system 120 coupled to the procedural sheath 10, the expandable structure 26 of the inner catheter 24 can be expanded using the syringe 50 (see FIG. 9B). The expandable structure 26 can be expanded until the inflation indicator 154 indicates the expandable structure 26 has been expanded to a pre-determined pressure. For example, the inflation indicator 154 can move from a first position to a second position when the expandable structure 26 is fully expanded. As shown in FIG. 9B, the inflation indicator 154 in the second position can protrude from a proximal end of the handle portion 130; however, the inflation indicator 154 can be positioned elsewhere on the handle portion 130. After the expandable structure 26 has been expanded, the inflation line 56 can be sealed by closing the valve 52. With the expandable structure 26 expanded, the closure system 120 and the procedural sheath 10 can be retracted until the expandable structure 26 abuts an inner surface of the vessel wall V.

The inner catheter 24 can be released from the outer catheter 22 by actuating or depressing the first actuator 132. As the inner catheter 24 is released, the procedural sheath 10 and the outer catheter 22 can also be retracted relative to the inner catheter 24 to expose the sealant 18 by simultaneously retracting the handle and the procedural sheath (see FIG. 9C). In this configuration, the handle portion 130 slides over the first actuator 132 to retract the outer catheter 22, while the inner catheter 24 remains in place. As the first actuator 132 is depressed and the handle body 130 is slid back, a visual indication 180 becomes visible through a window 182 that is exposed upon sliding the handle 130 proximally covering the first actuator 132 to display an image indicating whether the sealant has been properly deployed.

With the sealant 18 exposed, the support member 28 can be advanced to tamp the sealant 18 against an outer surface of the vessel wall V. Actuation or depression of the second actuator 134 can advance the support member 28 relative to the inner catheter 24 and the outer catheter 22. Additionally, the visual indicator 180 visible through the window 182 can display a different image that indicates the tamping of the sealant has been completed successfully and initiation of dwell period of sealant activation.

Figure 9E:
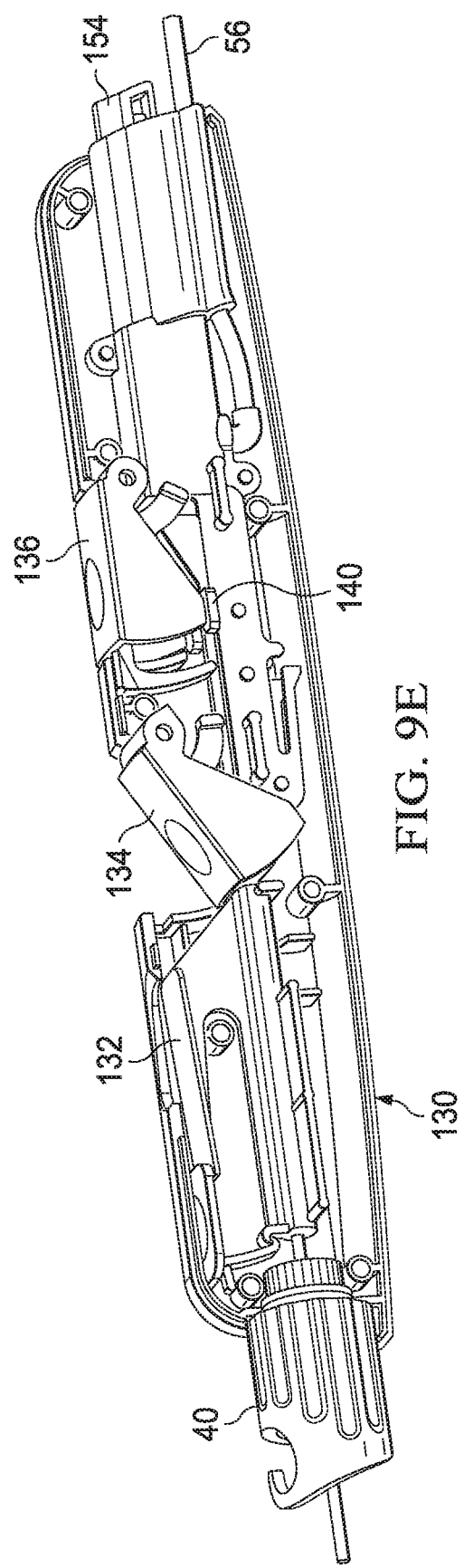

After the second actuator 134 has been depressed, but before the third actuator 136 has been depressed, the inflation indicator 154 can provide a lockout feature that prevents the third actuator 136 from being depressed while the expandable structure 26 is in an expanded configuration (see FIG. 9E). The inflation indicator 154 can extend through a proximal portion of the handle 130 such that a distal portion of the inflation indicator 154 is positioned below the third actuator 136. When the inflation indicator 154 is in the second position (e.g., extending beyond the proximal end of the handle 130) this not only indicates that the expandable structure 26 is inflated but further provides a blocking segment 140 integral with the inflation indicator 154 but internal to the handle body.

Figure 9F:
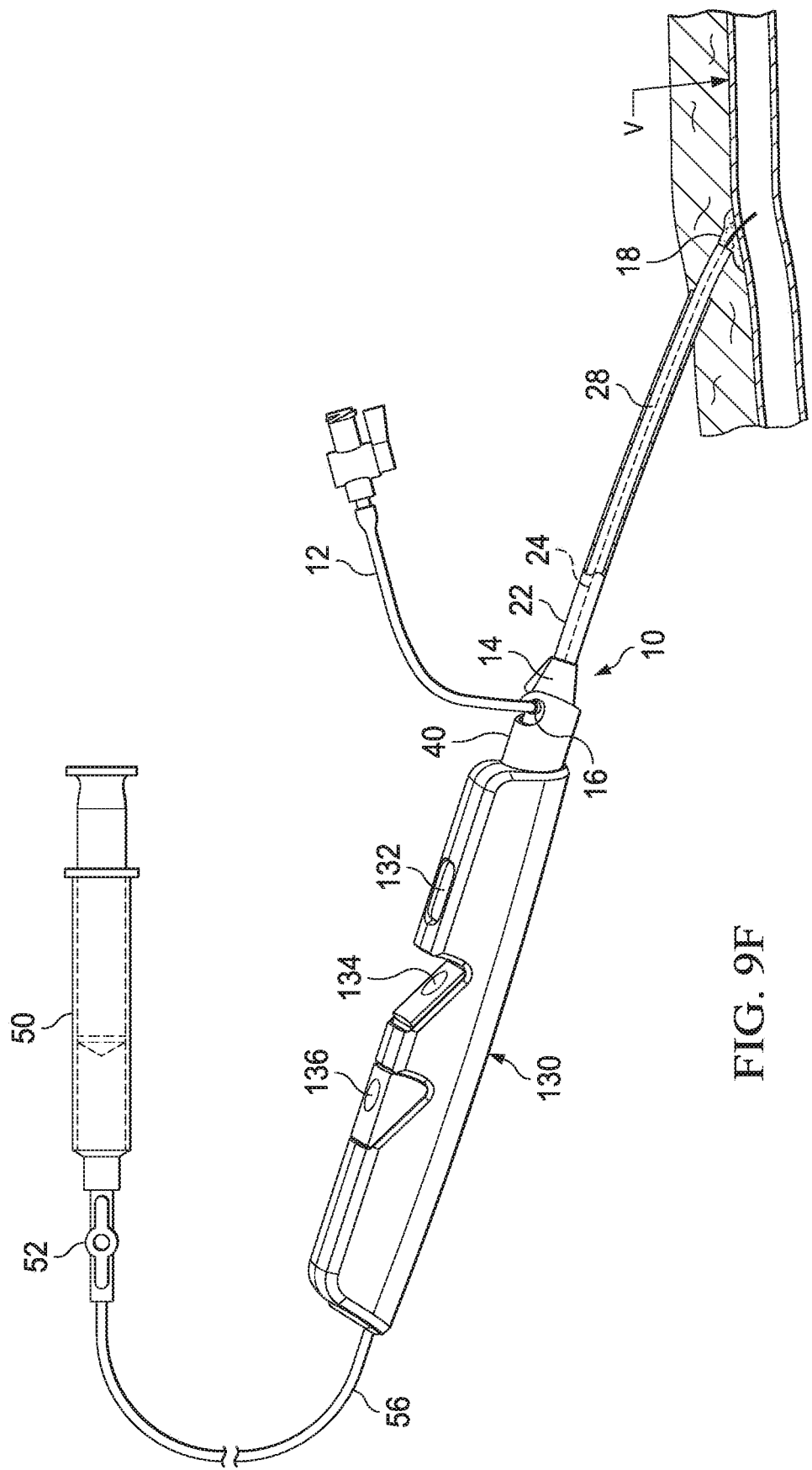
Figure 9G:
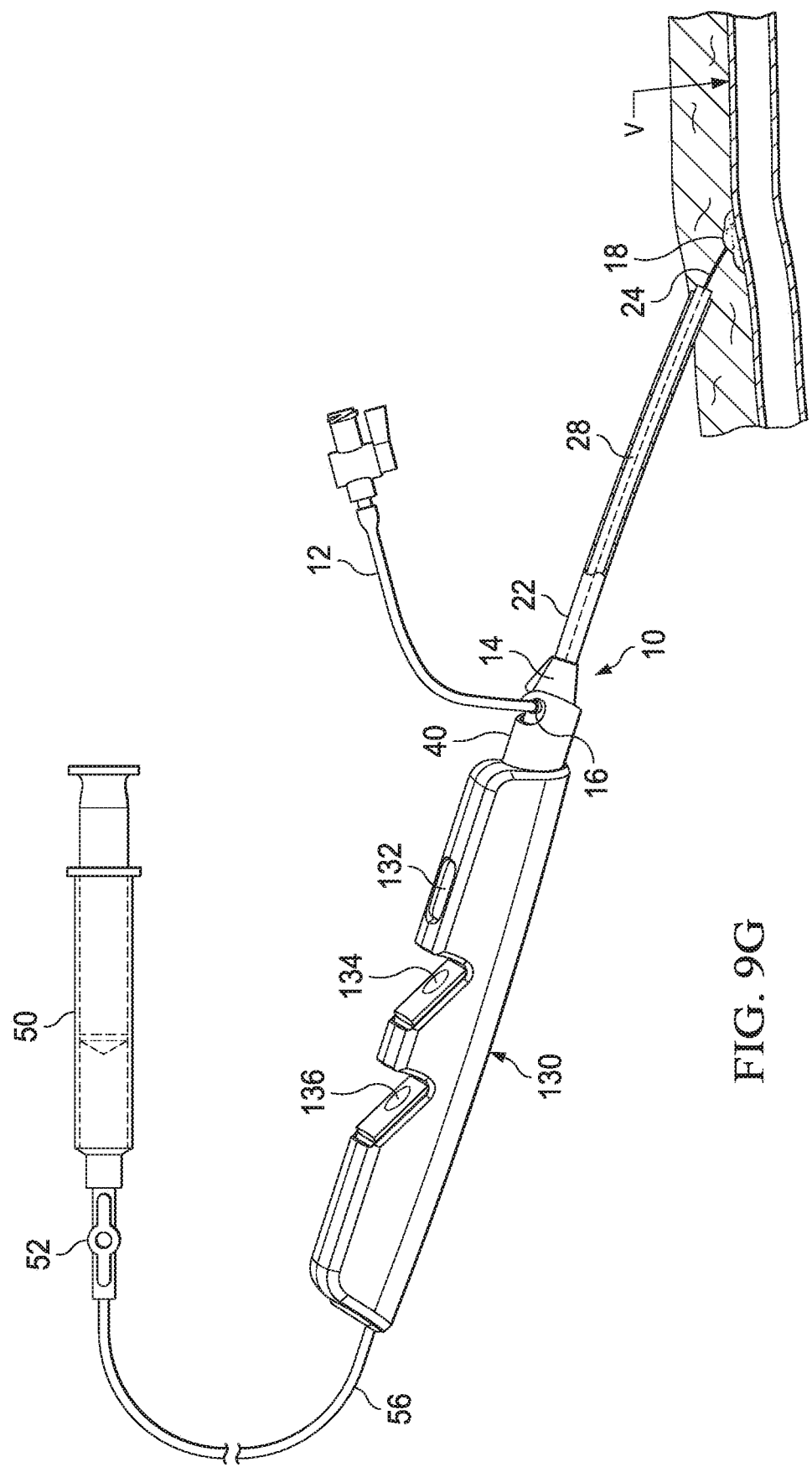

After the sealant 18 has been tamped, the expandable structure 26 can be contracted, for example, by opening the valve 52 and deflating the expandable structure 26 using the syringe 50 (see FIG. 9F). With the expandable structure 26 contracted, the expandable structure 26 can be retracted through the sealant 18 by actuating the third actuator 136. The inner catheter 24 can be retracted relative to the outer catheter 22 and/or support member 28 (see FIG. 9G). After the expandable structure 26 has been retracted through the sealant 18, the entire closure system 20 and procedural sheath 10 can be removed from the body, leaving the sealant 18 in place against the vessel wall V. Since the sheath adapter 40 is coupled to the procedural sheath 10, the closure system 20 and the procedural sheath 10 can be removed together, but the closure system 20 could be disengaged from the procedural sheath 10 and removed separately.

Figure 10A:
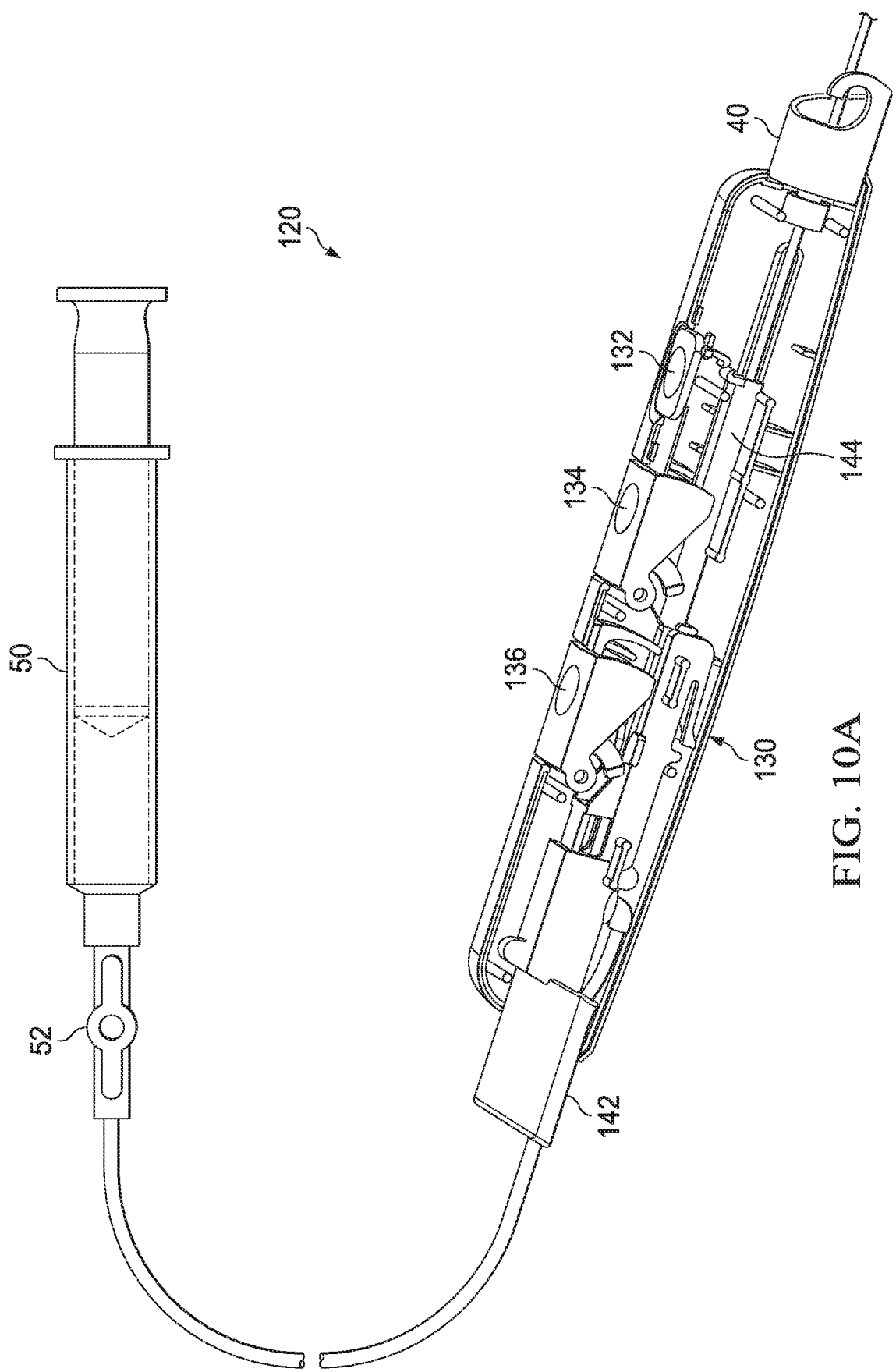
FIGS. 10A-10B illustrate an interior section close-up of a first actuator of the handle device shown in FIGS. 9A-9G.
Figure 10B:
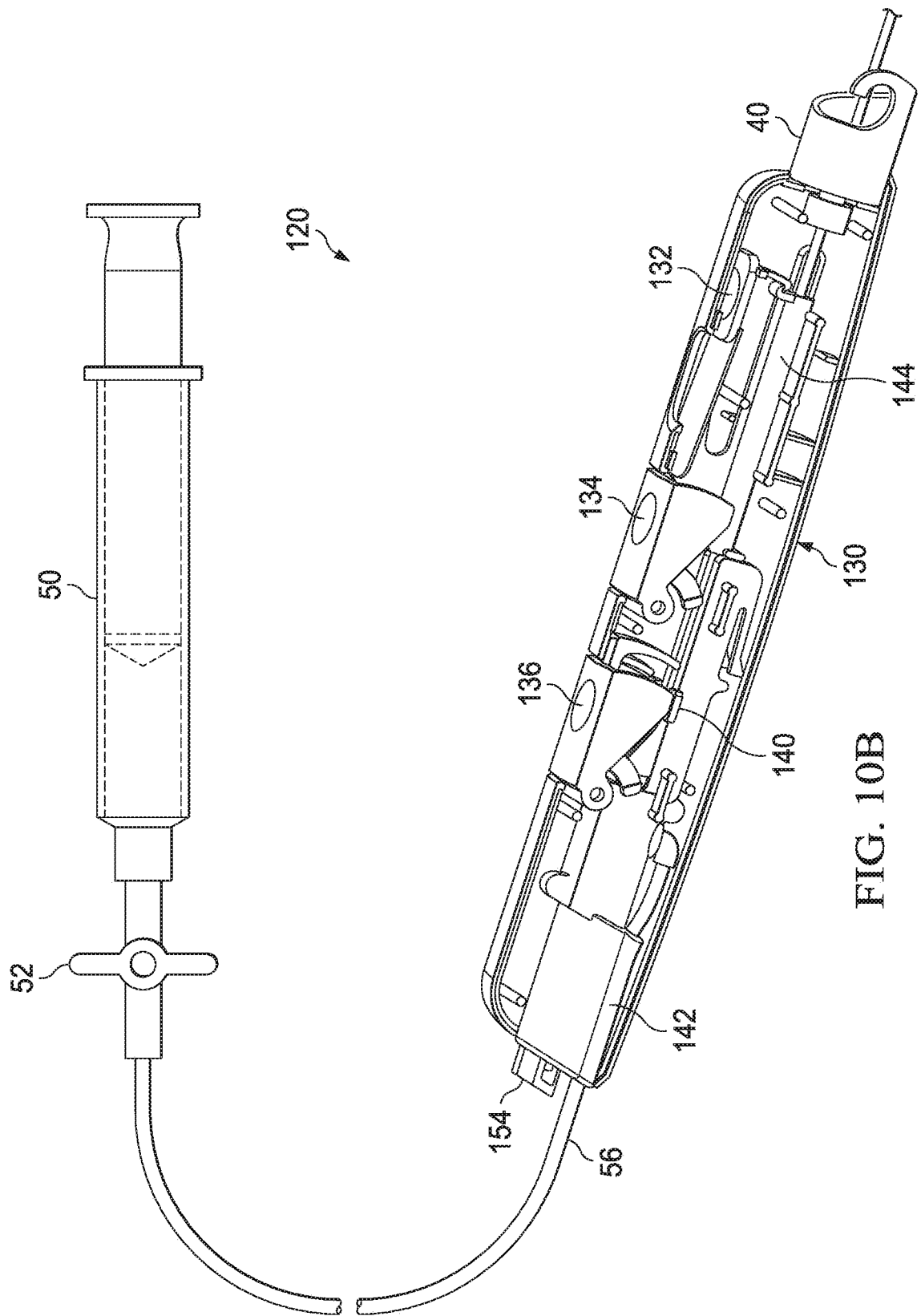

Turning now to FIGS. 10A-13B, the handle portion 130 of the closure system 120 is illustrated in further detail. The interior of the handle 130 contains a proximal 142 and distal 144 sled assembly that slides or glides within the interior of the handle as it is actuated, as shown in FIGS. 10A-10B. The distal sled assembly 144 can integrate the first actuator 132, such that when the first actuator is depressed and the handle is retracted, the distal sled assembly moves distally with respect to the handle, as shown in FIG. 10B. The proximal 142 and distal 144 sled assemblies are in a locked position with respect to the handle 130 until the first actuator 132 is fully depressed and locked into a second, depressed position. Upon depression of the first actuator 132, both distal sled assembly 144 and the proximal sled assembly 142 are unlocked and can move distally with respect to the handle body 130 when the handle is retracted. The proximal sled assembly 142 can house the inner catheter 24 and the inflation indicator.

Figure 10C:
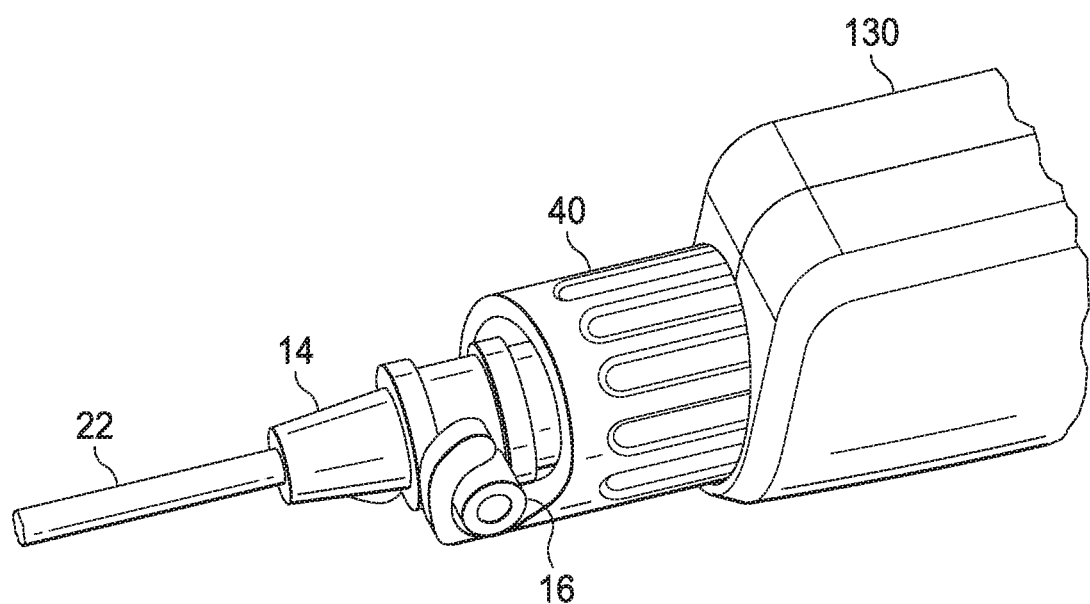
FIG. 10C illustrates a close-up view of a distal end of the handle device shown in FIGS. 9A-9G.

Turning to FIG. 10C, a close-up view of the device 120 is shown attached and locked with the procedural sheath at catch 40. The sheath catch or adaptor 40 can be oriented in any position or direction and, alternatively, can be provided such that it may be able to rotate about the handle 130 such that it can be adjusted to more easily catch the port or irrigation line of the procedural sheath.

Figure 11A:
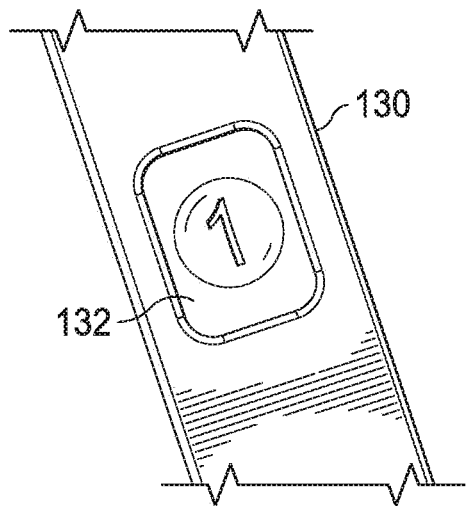
Figure 11B:
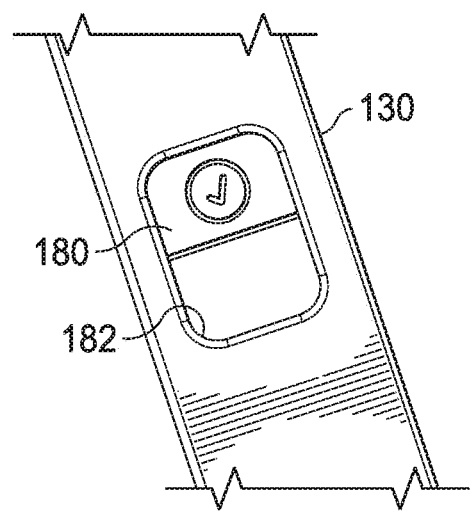
Figure 11C:
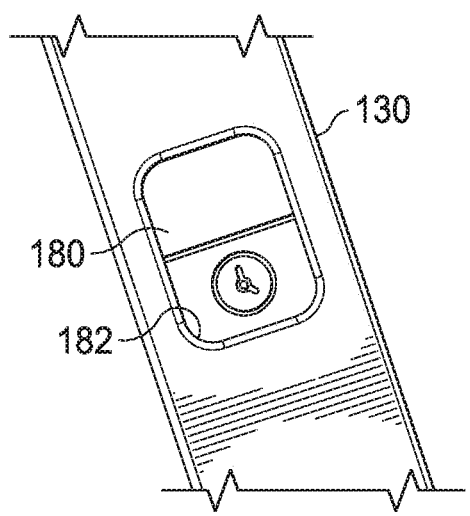

In addition to actuating the distal sled assembly, the first actuator 132 can also display a visual indication 180 through a window 182 that can provide a storyboard for the user to understand that the outer sleeve has been successfully retracted and the sealant deployed, as shown in FIGS. 11A-C. FIG. 11A shows a portion of the handle body 130 containing the first actuator, where the first actuator 130 can also optionally have a visual indication to identify that it is the first actuator in a series of actuators. Upon actuating or depressing the first actuator 132, a first image or visual indication can become visible and, for example, can display a symbol such as a check mark or other appropriate symbol through the window 182 to indicate that the sealant has been deployed, as shown in FIG. 11B. Once the second actuator 134 is also depressed, the storyboard can further display another image to convey that the sealant has been successfully tamped, as shown in FIG. 11C. Although a check mark and a circle with a symbol in it are shown, any visual indication or image may be used as appropriate to indicate the step completed.

Figure 12A:
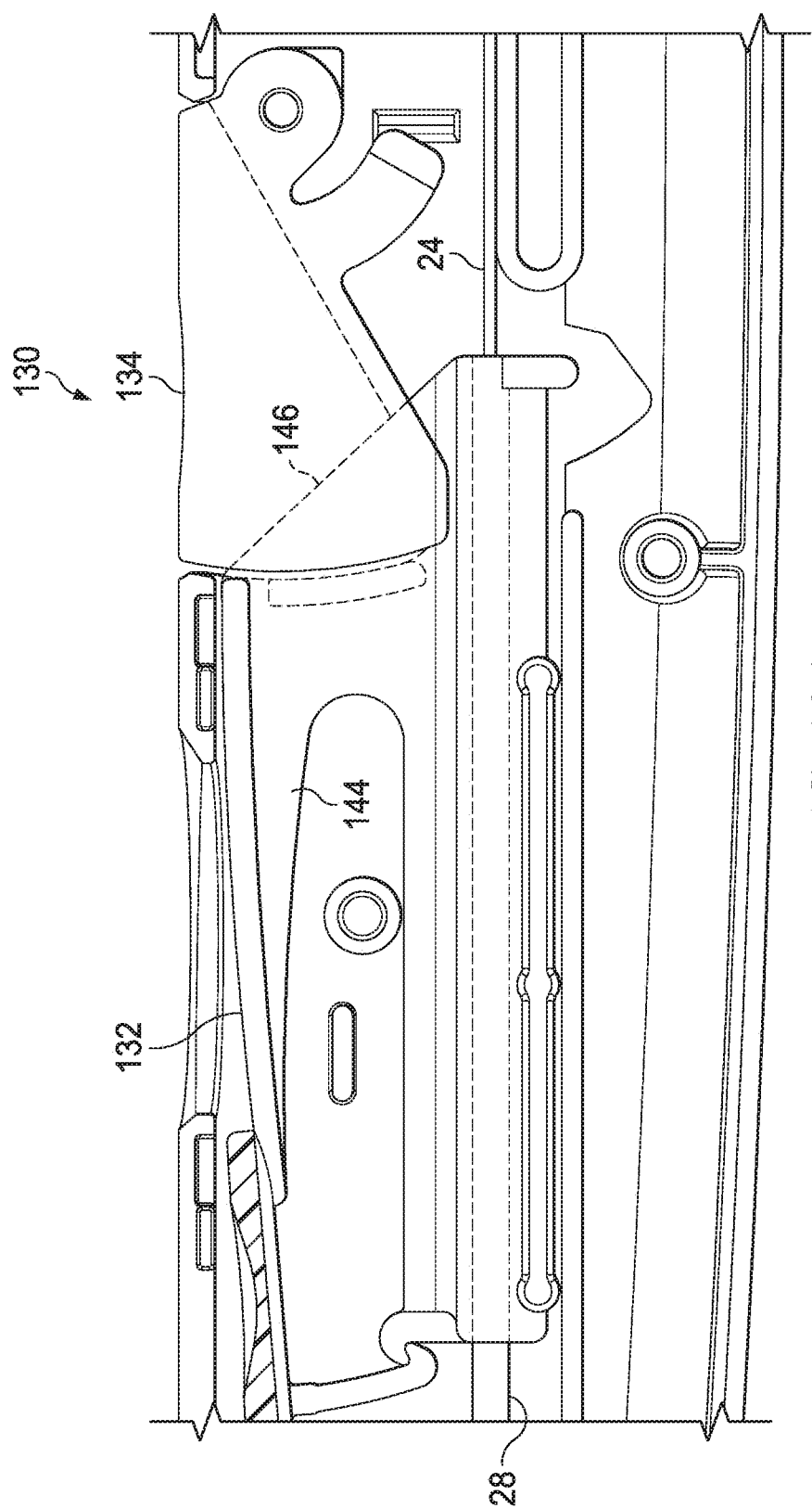
FIGS. 12A-12B illustrate an interior section close-up of a second actuator of the handle device shown in FIGS. 9A-9G.
Figure 12B:
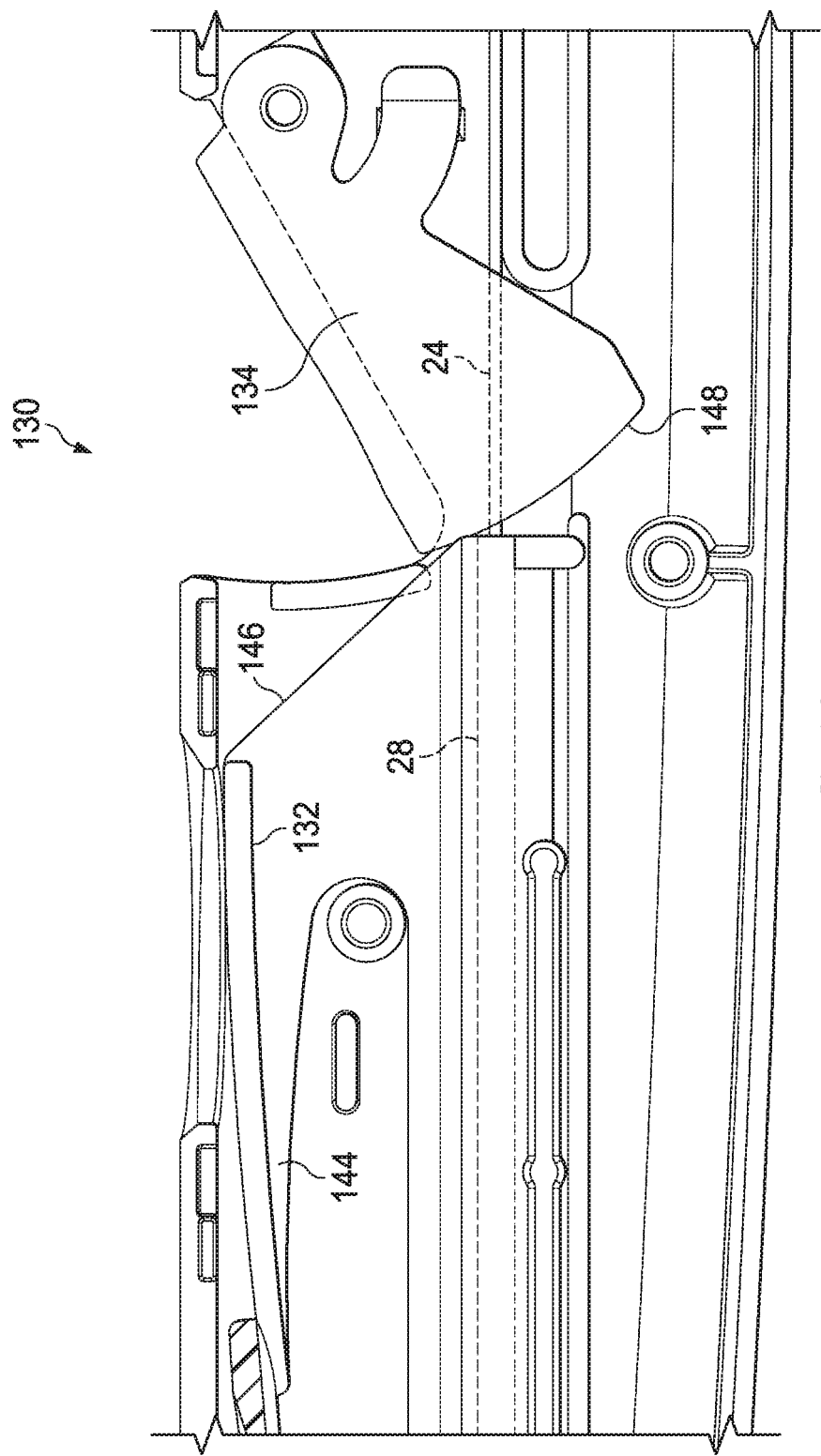

The second actuator 134 can include a cam drive mechanism, as shown in FIGS. 12A-12B, that can drive the distal sled assembly 144 associated with the first actuator 132 and support member 28 in a distal direction to tamp the sealant. The second actuator 134 can interface with a ramp 146 on the proximal end of the distal sled assembly 144/first actuator 132, which can be overmolded onto the support member 28 such that any distal movement of the distal sled assembly 144 can also move the support member 28 in a distal direction. When the second actuator 134 is depressed, the distal face 148 of the second actuator 134 can contact the ramp 146 of the distal sled assembly 144 pushing it in a distal direction and can advance the distal sled assembly 144 and the support member 28 in a distal direction causing the sealant to be compressed and tamped by advancement of the support member 28.

Figure 13A:
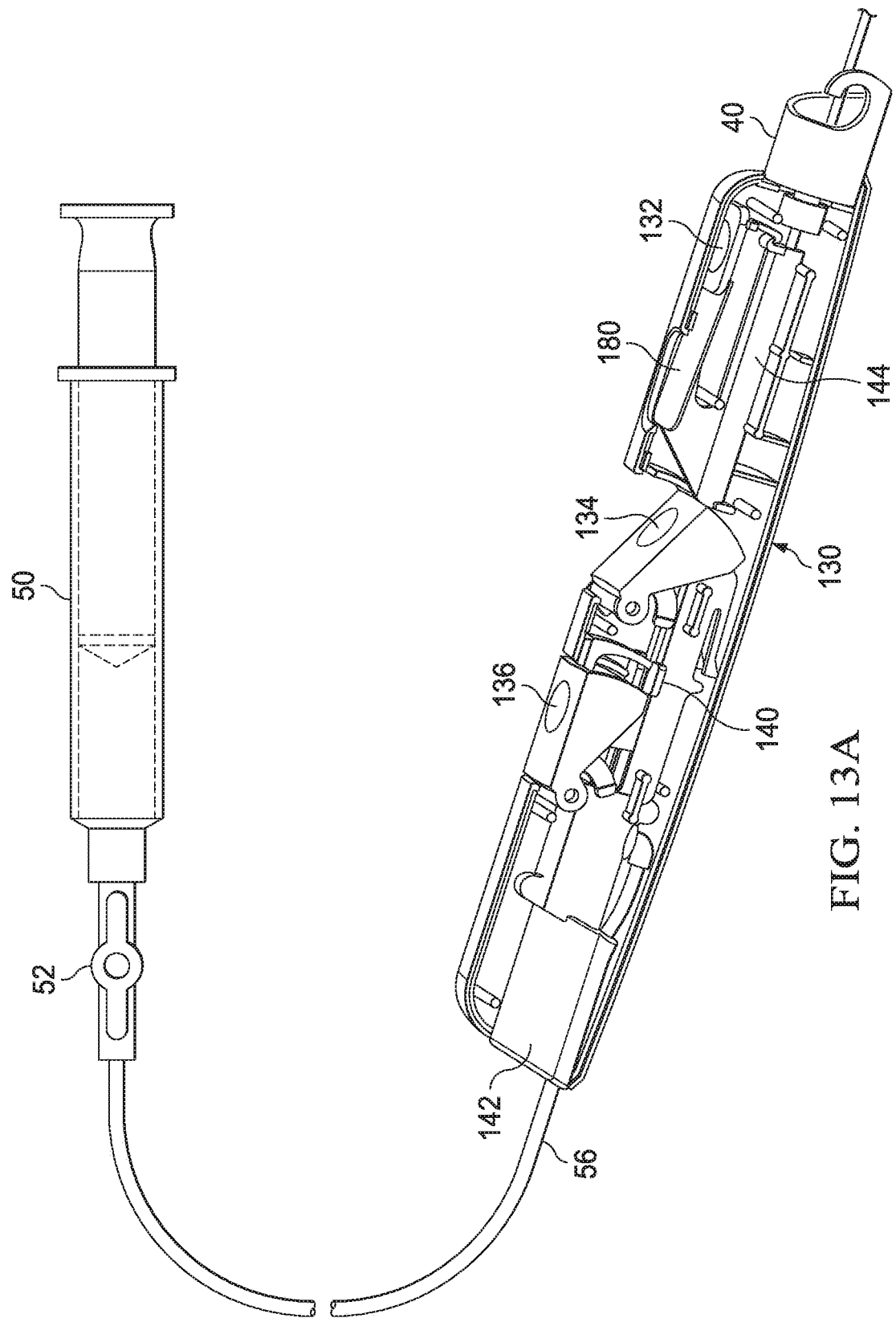
FIGS. 13A-13D illustrate an interior section close-up of a third actuator of the handle device shown in FIGS. 9A-9G.
Figure 13B:
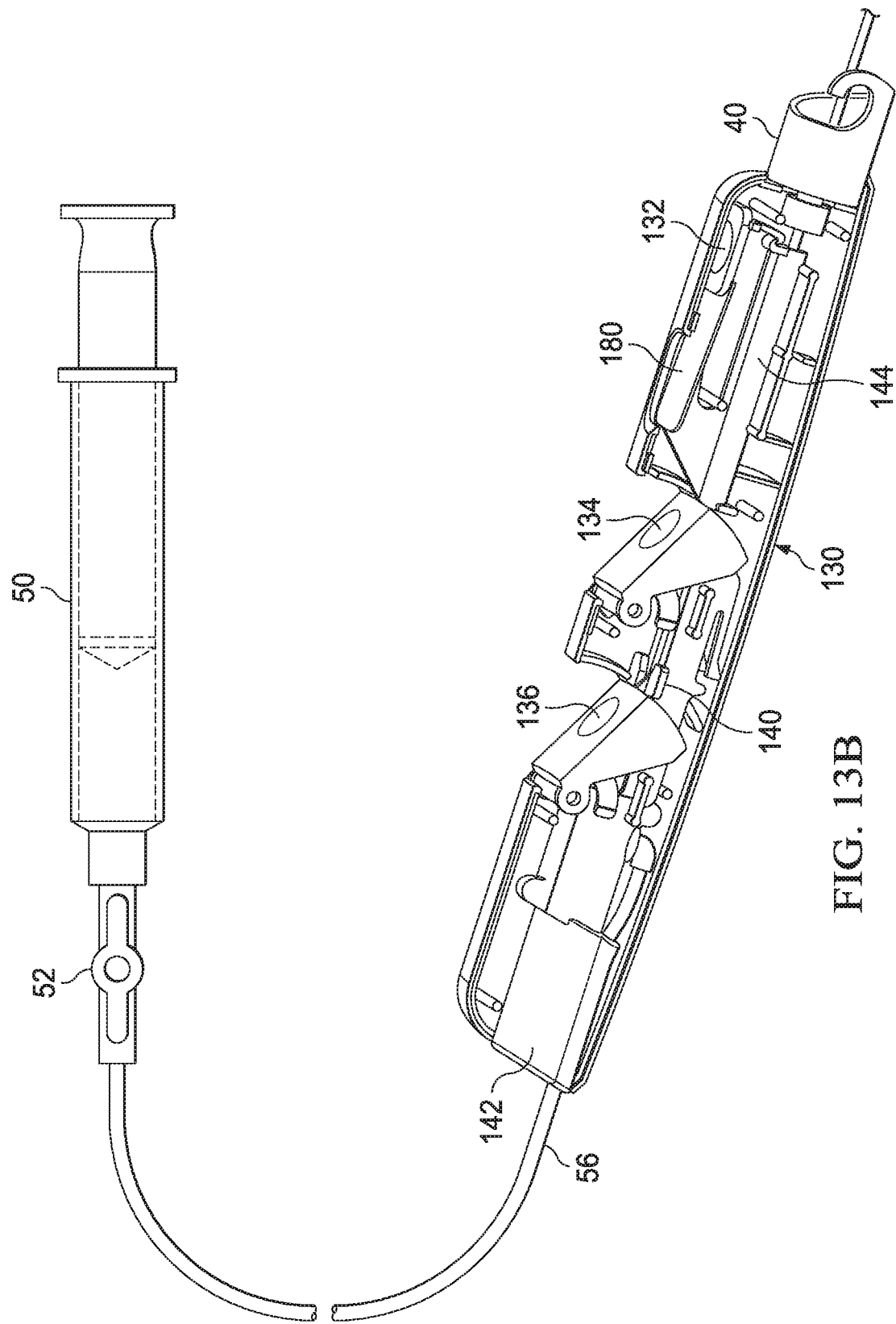
Figure 13C:
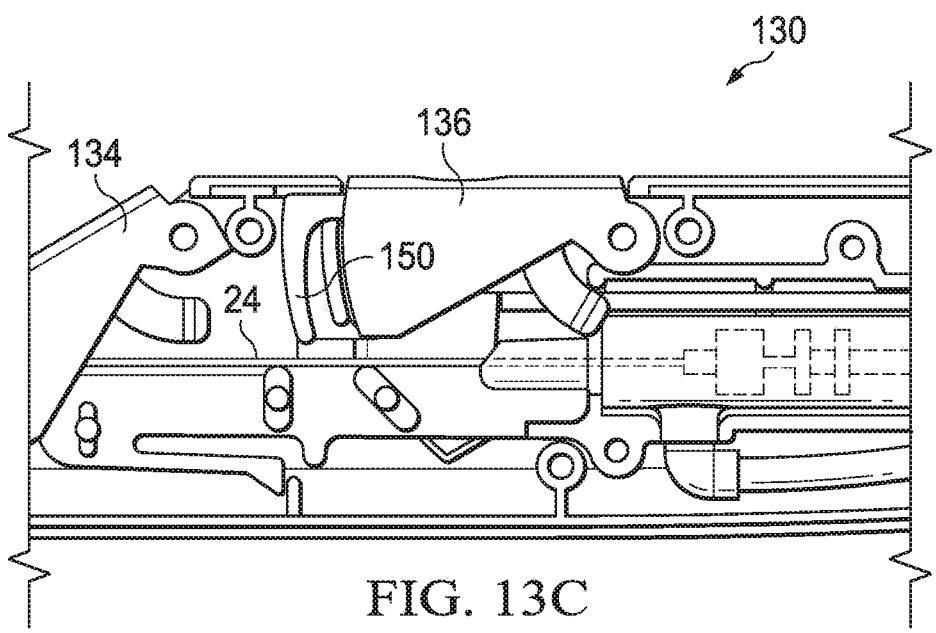
Figure 13D:
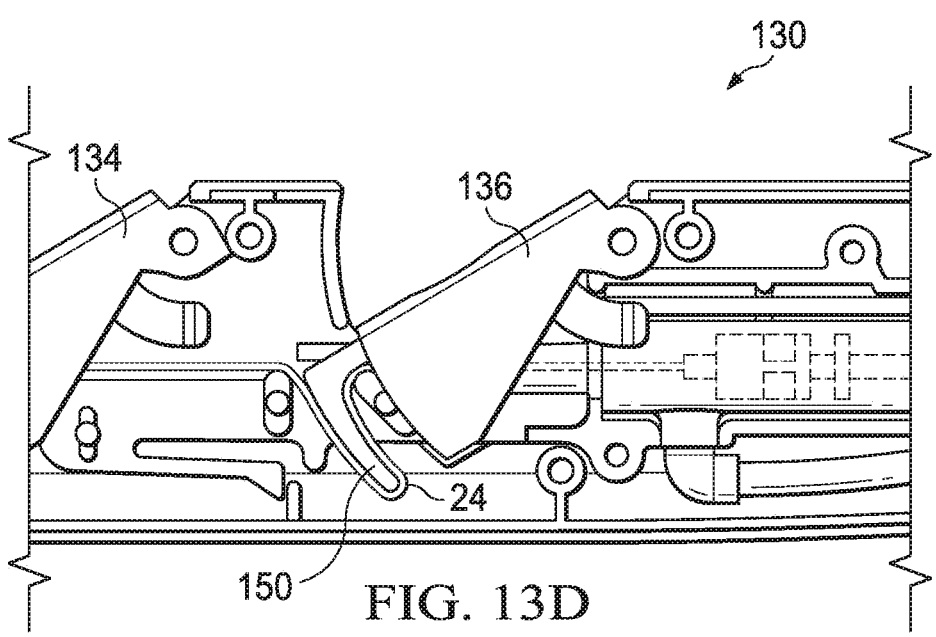

The third actuator 136 can be depressed to retract the deflated expandable structure 26 back into the support member 28, as seen in FIGS. 13A and 13B. In one aspect, the retraction of the expandable structure 26 can be accomplished by an arm 150, as seen in a further close-up interior view in FIGS. 13C and 13D, that extends from the third actuator 136 and below a top/outer surface of the third actuator 136. As the third actuator 136 is depressed, it can cause the arm 150 to engage with the inner catheter 24 and upon engaging the catheter, the arm can kink the inner catheter 24 on the proximal end, such that it can bend the catheter 24 away from a central axis of the handle 130, as seen in FIG. 13D, causing it to retract in the proximal direction, thereby causing the expandable structure 26 to retract into the support member 28.

In addition, if the expandable structure 26 is in an inflated state, as indicated by the inflation indicator 154 being extended beyond the proximal end of the handle 130, then the third actuator 136 cannot be depressed due to a lock-out feature. The lock-out feature is provided by a portion of the inflation indicator 154 that extends internally and distally into the handle 130 and further having protrusions 140 that extend axially outward away from the central axis of the handle 130 which act as a lock or stop that prevents the third actuator 136 from being depressed. When the expandable structure 26 is deflated, then the inflation indicator 154 can be shifted in a distal direction, such that it is no longer visible proximal to the handle. This motion of the inflation indicator 154 can also shift the position of the protrusions 140 that lock the third actuator 136 in place. Once shifted, the third actuator 136 is free to be depressed. This lockout feature provided by the inflation indicator 154 is beneficial in preventing an accidental depression of the third actuator 136 such that the expandable structure is not retracted prior to being fully deflated. In an alternative aspect, the lockout element can be a protrusion that extends axially toward the center of the handle 130 and locks out the distal arm on the third actuator 136 such that the third actuator 136 cannot be depressed.

An alternate embodiment of a closure system 220 is illustrated in FIGS. 14A-15D. In this embodiment, the closure system 220 can comprise two actuators that assist in deploying the sealant, tamping and retracting the expandable structure. Similar features to the first and second embodiments have similar reference numerals.

Similar to the function of the closure system 20 in FIG. 1B, the closure system 220 can be introduced through a procedural sheath (not shown) by introducing the outer catheter 22 through the hub portion 14 (not shown). The outer catheter 22 can be sized to be compatible with 5 F or larger standard procedural sheaths.

Figure 14A:
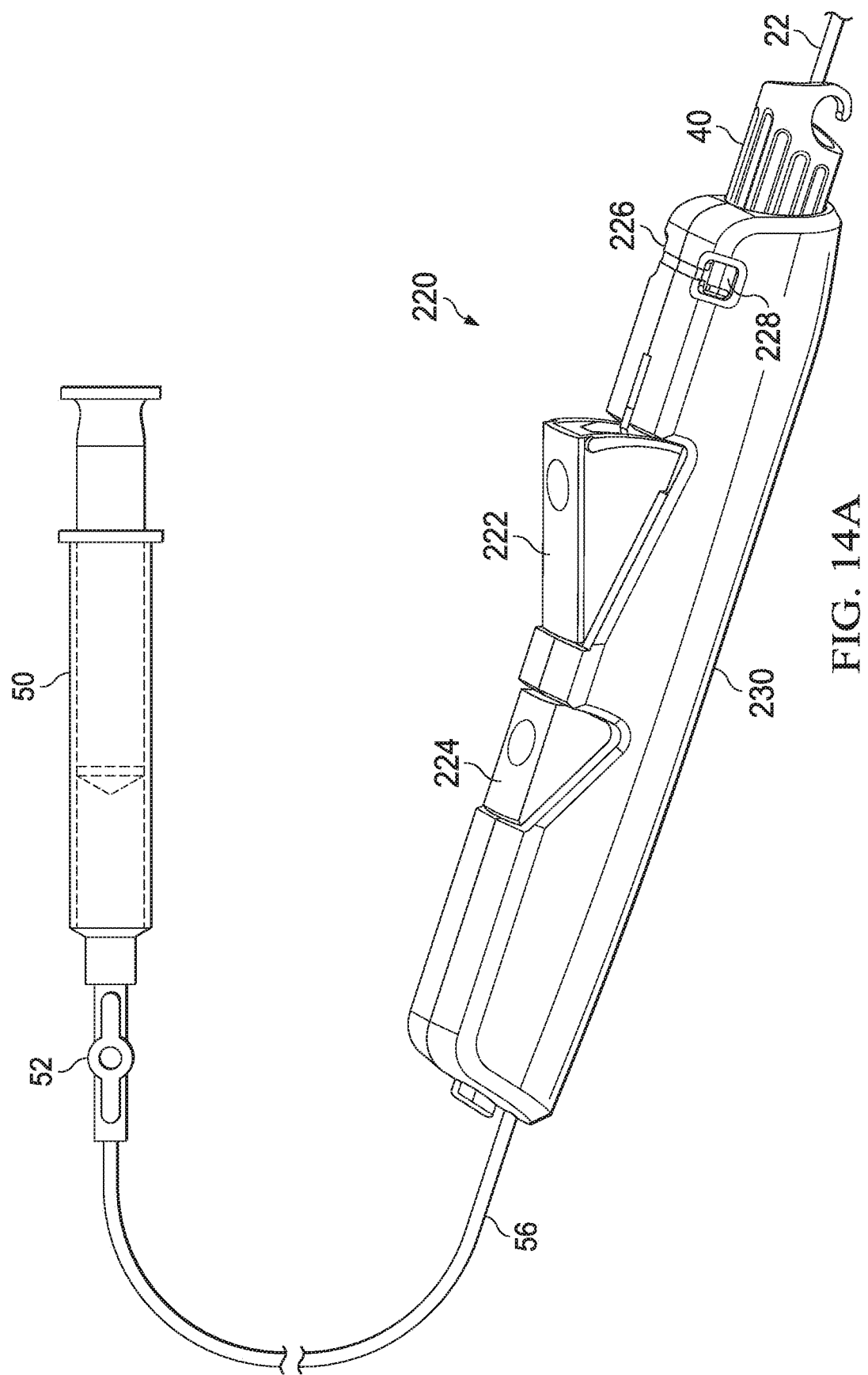
FIG. 14A illustrates a third embodiment of a closure system for delivering a sealant to an arteriotomy site.

As seen in FIG. 14A the handle 230 can contain at least one actuator and, in particular, two actuators. Although not shown, the closure system 220 can also be advanced through the procedural sheath until the sheath adaptor 40 engages the hub portion of the procedural sheath, just as in the previous embodiments. The closure system 220 can perform in a similar manner as the previous embodiments in regard to advancement through the procedural sheath and locking the handle via the sheath adaptor 40 to the procedural sheath.

Turning to FIG. 14A, the handle 230 is shown having a first actuator 222 and a second actuator 224. The first actuator 222 can have a combined function that both retracts the outer catheter 22 and tamps the sealant 18 when actuated. The second actuator 224 can have a function that is similar to the third actuators 36 and 136 from the previous embodiments. When the second actuator 224 is depressed, it can retract the expandable structure 26 into the support member or tube 28. Although FIGS. 14A-15D only show the closure device, the device can be employed in a similar manner as depicted in FIGS. 1B-1I and 9A-9G to effect a closure process in an arteriotomy.

Figure 14B:
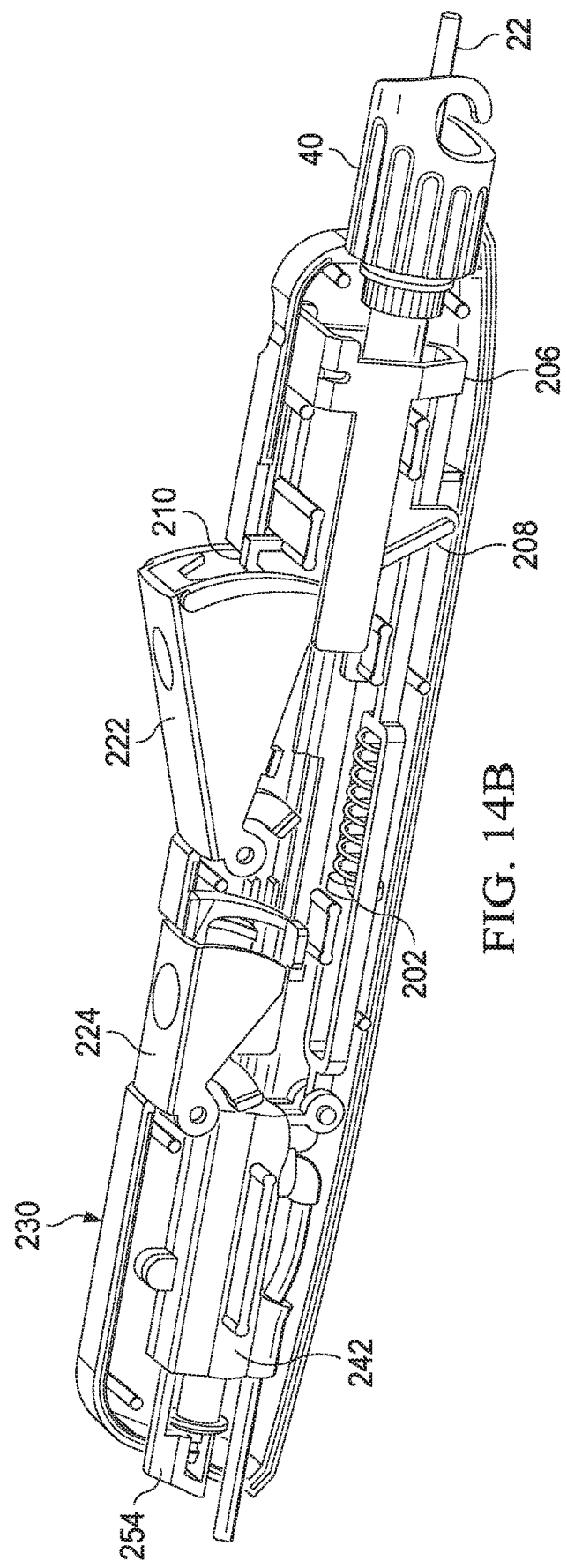
FIG. 14B illustrates an interior section view of the closure system of FIG. 14A.
Figure 14C:
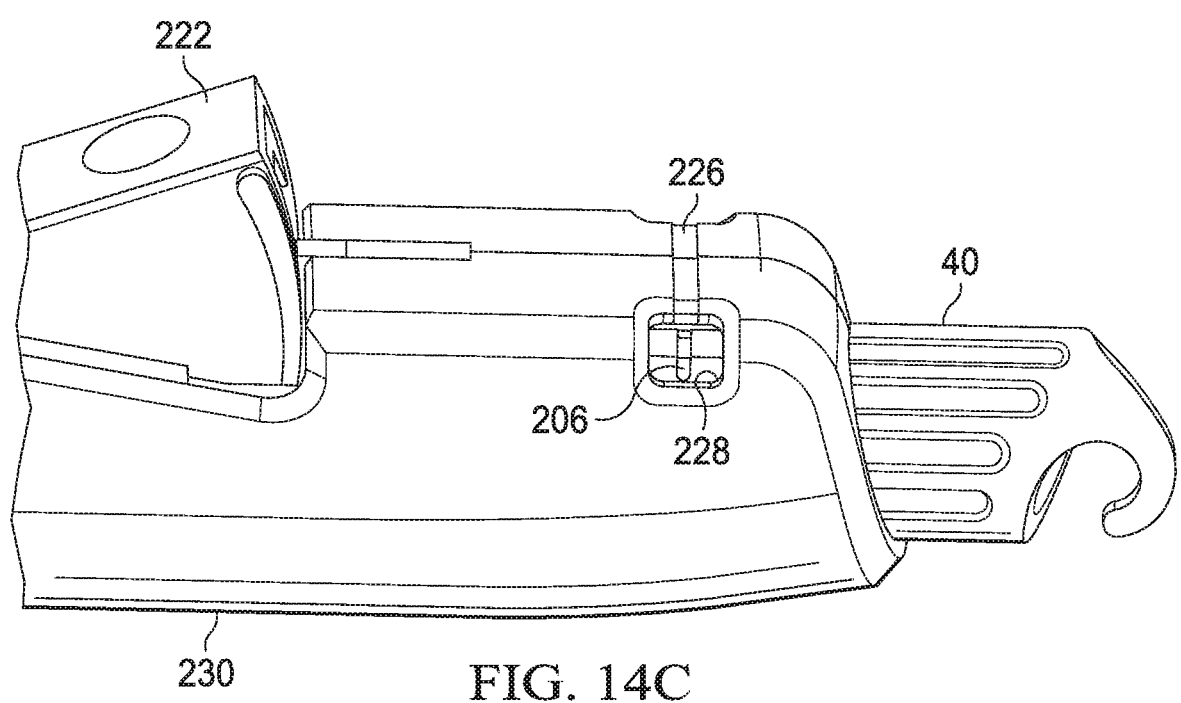
FIG. 14C illustrates a close-up view of a distal end of the handle device of FIG. 14A, further depicting a tension indicator.

Additionally, a tension indicator 206 can be incorporated into the handle 230 design, as shown in FIG. 14C, by including a tension indicator window 228 through which an illustration or image can be visible that indicates whether proper tension has been applied on the expandable structure 26 upon placement of the expandable structure 26 at the inner surface of the vessel wall, V. The tension indicator 206 can provide a visual cue to the user when the proper amount of tension has been applied to the expandable structure 26 prior to deploying the sealant 18. It is beneficial to know when the tension is appropriate because if excessive tension is exerted by the expandable structure 26 on the arterial wall it can cause the vessel to tent (e.g., distend) such that the artery is moved out of its initial position, e.g., its original anatomical position, during the closure process. If the sealant 18 is deployed with the artery in this tented position, then the tissue compression around the tented vessel may elicit a subtle separation of the hydrogel sealant 18 from the surface of the puncture site as the artery returns to its normal position after the expandable structure 26 is deflated and the device 220 is removed from the patient.

Turning to FIG. 14B, an internal view of the handle 230 is illustrated. The handle 230 can have a proximal sled assembly 242 that can house the inner catheter 24, similar to the other embodiments. When the expandable structure 26 is inflated in the patient's artery and pulled back to the arteriotomy, the expandable structure 26 can meet resistance when it is up against the vessel wall and the force exerted on the expandable structure 26 can be transferred back to the proximal sled assembly 242. The proximal sled assembly 242 can move in a distal direction when the expandable structure 26 is under tension, thereby compressing a tension spring 202 housed in the tension indicator 206. The tension indicator 206 can begin to move in a distal direction when the force on the expandable structure 26 exceeds the preload on the tension spring 202. The first actuator 222 can be depressed when a protrusion or black line on the tension indicator 206 lies within or is aligned with the proper tension zone 226 on the device handle 230, illustrating that the tension indicator 206 is in the appropriate position within the tension indicator window 228, as illustrated in FIG. 14C.

If the tension indicator 206 does not line up with the proper tension zone 226, then the first actuator 222 cannot be actuated or depressed, since the tension applied on the expandable structure 26 is not in the proper tension zone (e.g., black band). Thus, the tension indicator zone 226 can include lockout features that can prevent the first actuator 222 from being depressed when improper tension is applied via the expandable structure 26. The tension zone 226 can be indicated in any manner and, in the embodiment shown in FIG. 14C, it is indicated by a black line marked on the handle device 230. The position of the black line on the handle 230 is positioned in the proper tension zone. The tension indicator 206 can be a sliding piece inside of the handle assembly 230 that can slide distally based upon the tension applied on the expandable structure 26. Therefore, to ensure correct tension is being applied to the expandable structure 26, the user can adjust the tension upon the expandable structure 26 until the black line on the tension indicator 206 is aligned with the black line on the handle of the tension zone 226. The tension can be adjusted, in one aspect, by pulling back or letting up on the handle of the closure device, whichever is necessary. Alternatively, any other visual indication system may be used as appropriate to indicate proper tension applied to the expandable structure 26.

Figure 15A:
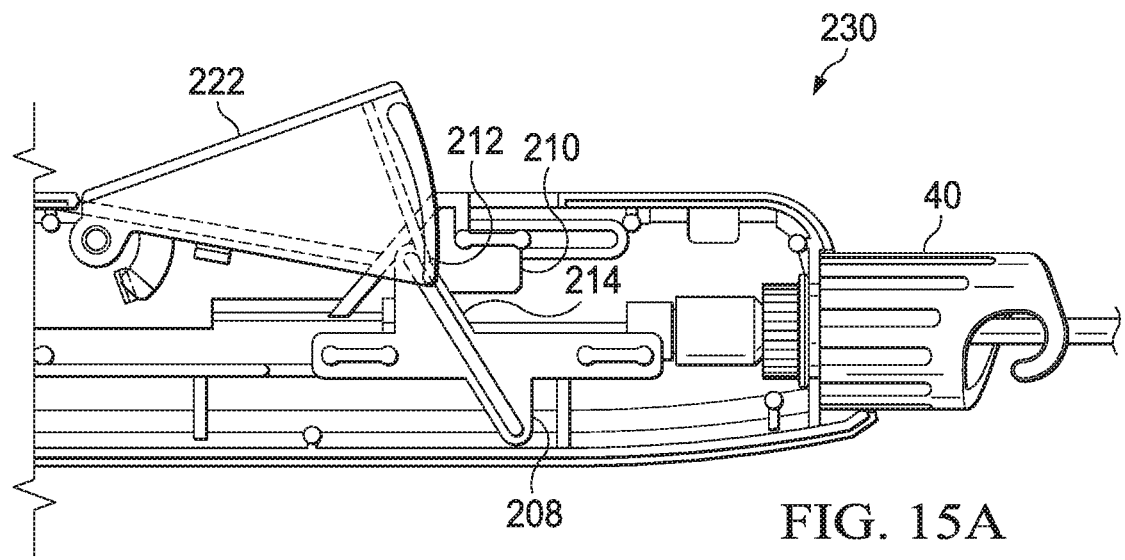
FIGS. 15A-15D illustrate interior section views of the first actuator of the closure system in FIG. 14A.

Turning to FIGS. 15A-D, an internal view of the handle housing is shown, these views do not show the tension indicator 206, however, it can be included if desired as shown in FIGS. 14A-C. FIG. 15A illustrates the handle 230 at rest, before the first actuator 222 has been depressed. It can be seen that in the rest position, an inner rib 212 on the first actuator 222 can engage with or contact a ramp 214 on the pull rack 208. The pull rack 208 can be connected to the outer sleeve assembly 62 (not shown). As the first actuator 222 is actuated or depressed the pull rack 208 can begin to shift in a proximal direction, e.g., away from the sheath adaptor 40. As the pull rack 208 shifts in a proximal direction by actuation of the first actuator 222, the outer sleeve 62 also begins to shift in a proximal direction, thus, exposing the sealant in the tissue tract next to the arteriotomy. As the first actuator 222 is being initially depressed, as in FIG. 15B, the sealant can begin to be exposed by retraction of the sleeve.

Figure 15B:
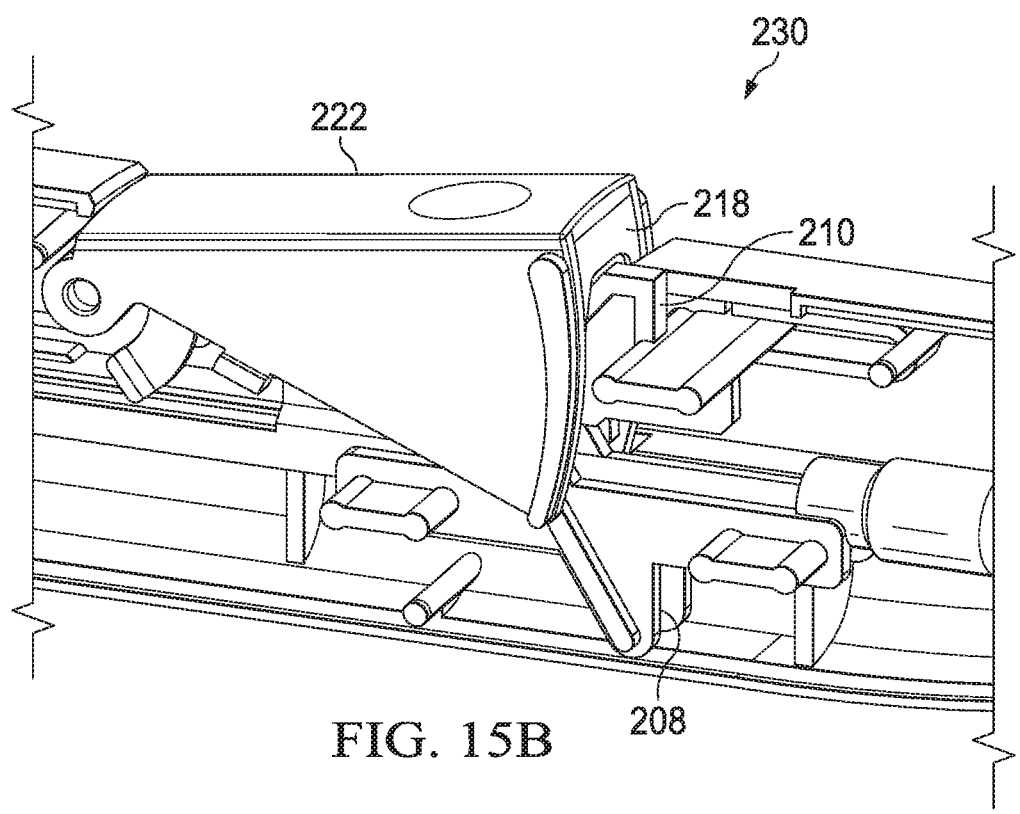

As the first actuator 222 is depressed partially, as in FIG. 15B, the distal face 218 of the first actuator 222 can engage with the push rack 210 and can begin to shift the push rack 210 in a distal direction, e.g., toward the sheath adaptor 40, at a point that the sealant is at least partially exposed and, in one aspect, is exposed about 50%. The push rack 210 can be connected to the support member 28, or tamp tube, such that when the push rack 210 is shifted in a distal direction it is also shifting the support member 28 in a distal direction effectively tamping the sealant against the vessel wall of the arteriotomy. After about 50% of the sealant is exposed by the movement of the pull rack 208 (e.g., as the first actuator is being initially depressed), both the push rack 210 and pull rack 208 can move in their respective directions simultaneously or relatively simultaneously revealing the sealant and tamping the sealant. It is preferable that at least a portion of the sealant be exposed prior to tamping; this can help to mitigate jamming of the sleeve and/or sealant. In this embodiment, about 50% of the sealant is exposed before the push rack 210 is engaged, however, any other appropriate amount of the sealant can be exposed that is less than or greater than 50% before engaging the push rack 210.

Figure 15C:
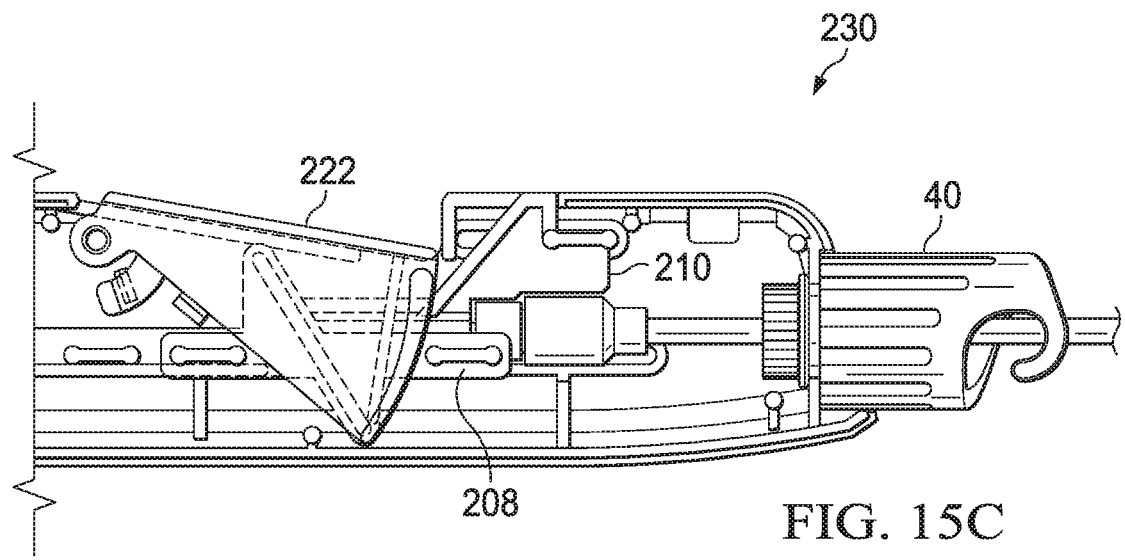
Figure 15D:
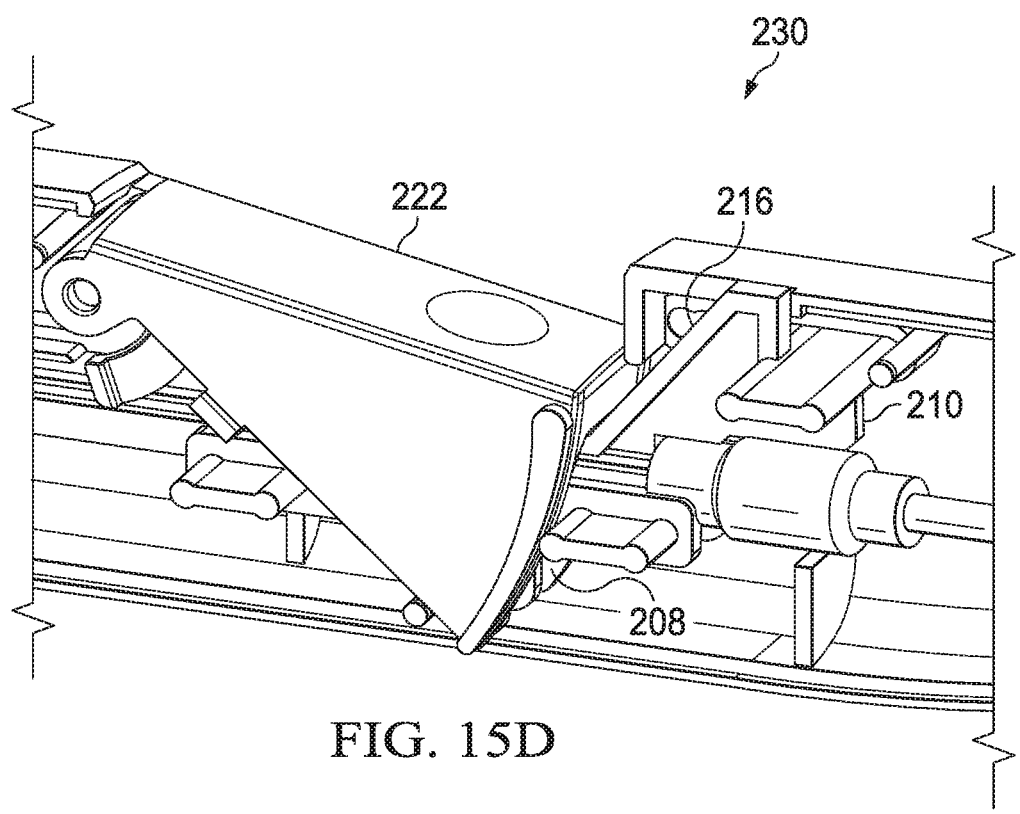

In FIG. 15C, the pull rack 214 is shown in its final position, shifted proximal to where it began, while the push rack 216 is shown in its final position, shifted distal to where it began. FIG. 15D shows the first actuator 222 fully depressed with the ramp 216 on the push rack 210 exposed internal to the handle 230. The first actuator 222, or combination actuator, can drive the pull rack 208 and the push rack 210 utilizing a cam drive mechanism similar to the previous embodiment. The first actuator 222 can include features that engage with each rack and can drive them in the desired direction.

Although not illustrated, depressing the second actuator 224 can retract the expandable structure 26 similar to how the third actuator functions in the previous embodiments and can also further include a lockout mechanism that can prevent the second actuator 224 from being depressed if the expandable structure 26 is still inflated, as indicated by the inflation indicator 254. This lockout feature is similar to that described above in regard to the second embodiment having a blocking segment or protrusions 140 extending from the proximal sled assembly and as shown in FIGS. 10A, 10B, 13A and 13B.

This embodiment illustrates a handle device 230 having two actuators, however, the handle can have more or less actuators than that described herein. For instance, the handle can be provided with only one actuator that carries out all of the functions described herein or one actuator that carries out one or more functions while another method is employed for any remaining functions. Thus, the handle on the closure device can have one or more actuators, as appropriate.

Figure 3:
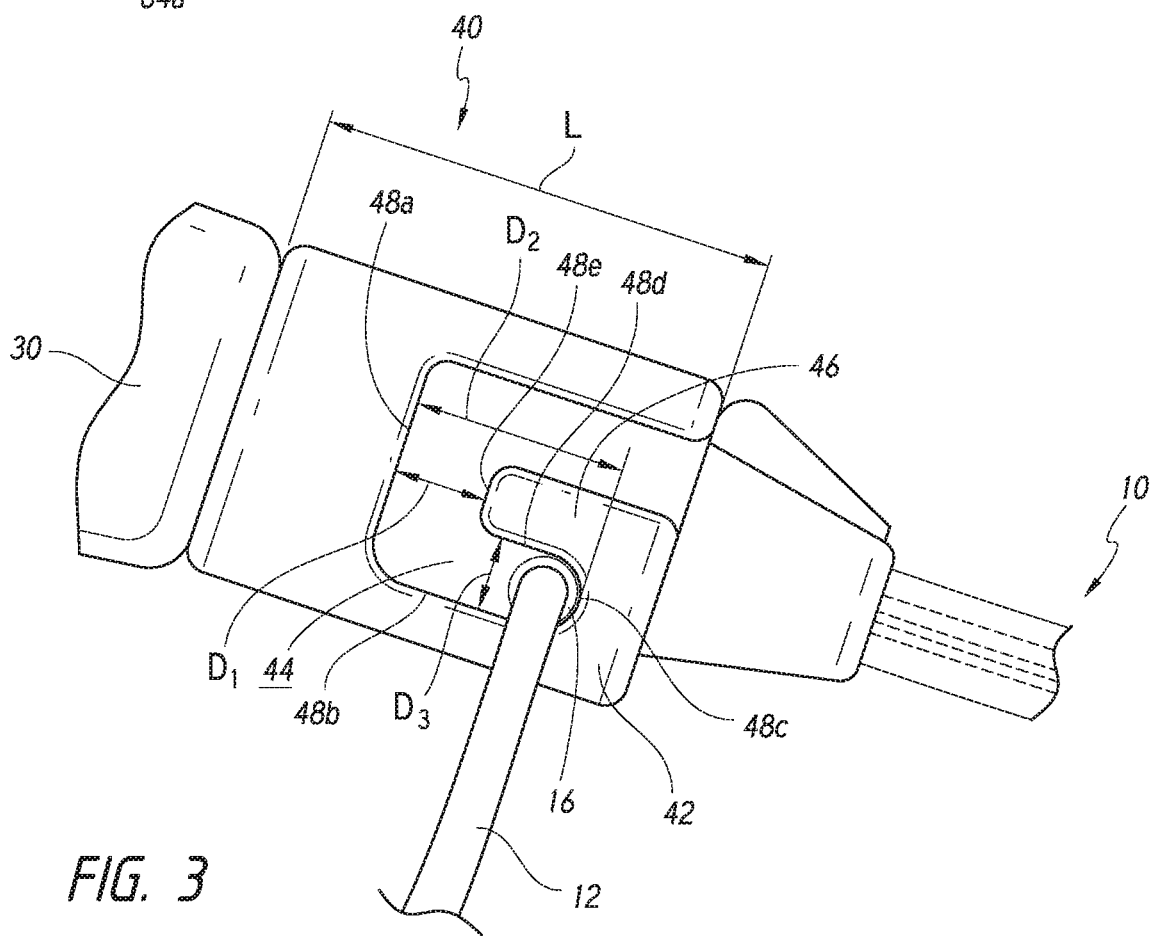
FIG. 3 illustrates an enlarged view of a sheath adapter of the closure system shown in FIG. 1C taken through line 3-3.

FIG. 3 illustrates an enlarged view of the sheath adapter 40 that can engage any sheath having a side port or irrigation line. The sheath adapter 40 can be integral with the handle portion 30 or a separate component coupled to the handle portion 30, either directly or via an intervening catheter shaft or other linking structure.

As shown in FIG. 3, the sheath adapter 40 can have any shape that is appropriate and, in particular, can have a generally tubular, cylindrical or generally frustoconical shape. The sheath adaptor 40 can include polycarbonate, ABS, silicone, an elastomer, or other suitable materials. An elastomeric material may be beneficial to enable the sheath adapter 40 to grip the side port 16 or irrigation line 12 of the sheath 10.

The sheath adapter 40 can include an attachment structure that can releasably attach to a procedural sheath, such as a bayonet connector or hook portion 42 that can hook around a transverse retention surface such as a distally facing surface on the side port 16 or irrigation line 12 of a procedural sheath 10. The hook portion 42 can form a passageway 44 that can guide the side port 16 or irrigation line 12 into engagement with the sheath adapter 40. The hook portion 42 can be shaped such that both axial and rotational movement is required to disengage the hook portion 42 from the sheath 10.

The passageway 44 can be defined by a distal facing edge 48a, an outer lateral edge 48b, a proximal facing edge 48c, an inner lateral edge 48d, and a hook end edge 48e. The edges defining the passageway 44 can be generally straight or curved. The distance $D_1$ between the distal facing edge 48a and the hook end edge 48e can be sized to permit the side port 16 or irrigation line 12 to enter the passageway 44. For example, the distance $D_1$ can be within about 10% or within about 20% of a diameter of the side port 12 or the irrigation line 12, which can be between about 3 F and about 11 F, such as between about 3 F and about 6 F, between about 5 F and about 8 F, or between about 7 F and 10 F, including about 3F, 4 F, 5F, 6 F, 7F, 8 F, 9F, 10 F, or 11 F.

The distance $D_1$ can be less than the distance $D_2$ between the distal facing edge 48a and the proximal facing edge 48c (less than about 60 percent of $D_2$, less than about 50 percent of $D_2$, less than about 40 percent of $D_2$, less than about 30 percent of $D_2$, less than about 20 percent of $D_2$, or otherwise).

The distance $D_3$ between the outer lateral edge 48b and the inner lateral edge 48d can be sized to receive the side port 16 or irrigation line 12 of the procedural sheath 10. For example, the distance $D_3$ can be within 10% of a diameter of the side port 16 or irrigation line 12, which can be between about 3 F and about 11 F, such as between about 3 F and about 6 F, between about 5 F and about 8 F, or between about 7 F and 10 F, including about 3F, 4 F, 5F, 6 F, 7F, 8 F, 9F, 10 F, or 11 F. The distance $D_3$ can be less than the distance $D_1$.

The inner lateral edge 48d can have a length suitable to block the side port 16 or irrigation line 12 from disengaging from the sheath adapter 40 when the closure system 20 is rotated. For example, the length of the inner lateral edge 48d can be at least as long as a diameter of the side port 16 or the irrigation line 12. The length of the inner lateral edge 48d can be at least about 20% of a length L of the sheath adapter 40, at least about 30% of a length L of the sheath adapter 40, or at least about 40% of a length L of the sheath adapter 40. The length of the inner lateral edge 48d can be at least as long as the distance $D_3$.

Although not shown, in some embodiments, the distance $D_3$ can narrow from the proximal facing edge 48c toward the hook end edge 48e. The hook portion 46 can be spring-like and move away from the outer lateral edge 48b to enlarge the distance $D_3$ between the outer lateral edge 48b and inner lateral edge 48d to permit the side port 16 or irrigation line 12 to move toward the proximal facing edge 48c. The hook portion 46 can rebound back toward the outer lateral edge 48b to retain the side port 16 or irrigation line 12.

Figure 4:
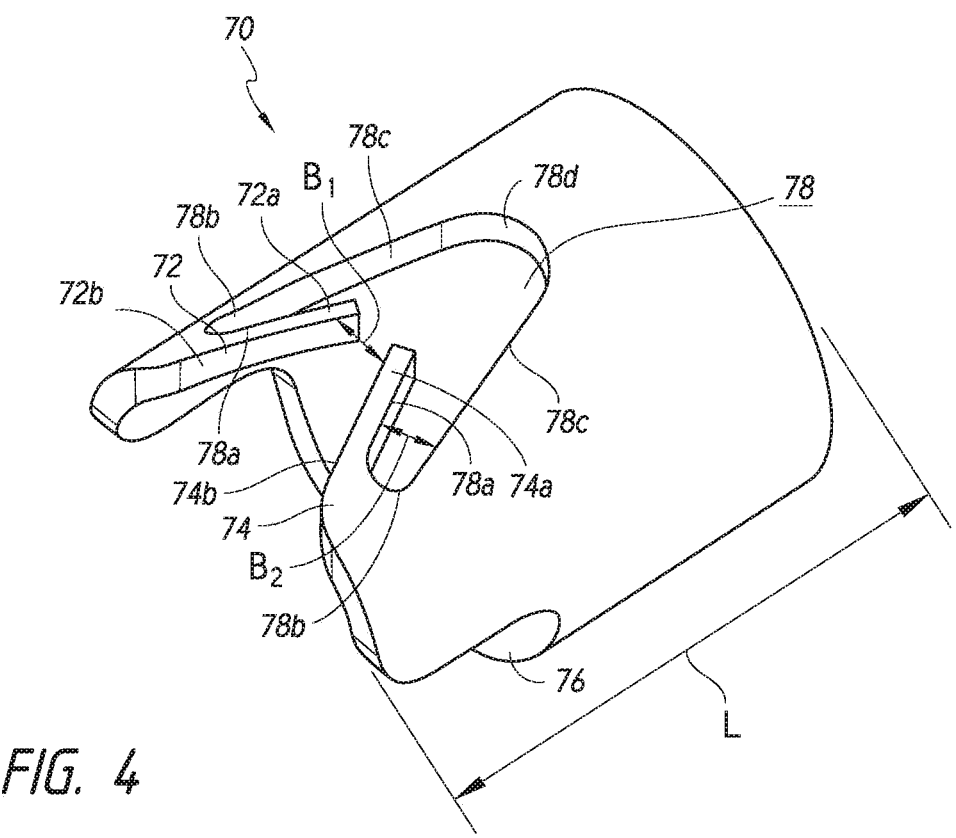
FIG. 4 illustrates another embodiment of a sheath adapter that can be used with the closure system shown in FIGS. 1A-1I.

FIG. 4 illustrates an enlarged view of another sheath adapter 70 that can be used with the closure system 20 to engage any sheath having a side port or irrigation line. The sheath adapter 70 can be integral with the handle portion 30 or a separate component coupled to the handle portion 30.

As shown in FIG. 4, the sheath adapter 70 can have a generally cylindrical or generally frustoconical shape. The sheath adaptor 70 can include polycarbonate, ABS, silicone, an elastomer, or other suitable materials. An elastomeric material may be beneficial to enable the sheath adapter 40 to grip the side port 16 or irrigation line 12 of the sheath 10.

The sheath adapter 70 can include an attachment structure (e.g., a bayonet connector) that can releasably attach to a procedural sheath. For example, the attachment structure can include a first hook portion 72 having a first hook end portion 72a and a second hook portion 74 having a second hook end portion 74a. At least a portion of the first and second hook portions 72, 74 can extend distally beyond a distal facing edge 76 of a remaining portion of the sheath adapter 70.

The first hook portion 72 and the second hook portion 74 can be generally the same shape and size but inverted relative to each other, such that lower surfaces 72b, 74b of the first and second hook portions 72, 74 are tapered inward and toward each other to guide the side port 16 or irrigation line 12 toward a passageway 78. The sheath adapter 70 can be generally symmetrical across a plane extending between the first and second hook portions 72, 74 and through the longitudinal axis of the sheath adapter 70.

A distance $B_1$ between a first hook end portion 72a and a second hook end portion 74a can be less than a diameter of the side port 16 or irrigation line 12 to prevent the side port 16 or irrigation line 12 from inadvertently detaching from the sheath adaptor 70. The hook ends 72a, 74a can bend to enlarge the distance $B_1$ to allow the side port 16 or irrigation line 12 to enter the passageway 78, but then rebound once the side port 16 or irrigation line 12 is in the passageway 78 such that the side port 16 or irrigation line 12 is retained between the hook ends 72a, 74a and the distal facing edge 78d. The spring-like hook ends 72a and 74a can be designed to retain the side port 16 or irrigation line 12 under normal use but can be overcome by the user if detachment of the sheath adapter 70 is necessary.

Each hook portion 72, 74 can define a portion of the passageway 78. Each hook portion 72, 74 can have an inner lateral edge 78a, a proximal facing edge 78b, an outer lateral edge 78c, and a distal facing edge 78d. The edges defining the passageway 78 can be generally straight or curved.

The distance $B_2$ between the inner and outer lateral edges 78a, 78c can be sized to permit the necessary bending of the hook portions 72, 74 toward their respective outer lateral edge 78c to allow the side port 16 or irrigation line 12 to enter the passageway 78.

Figure 5:
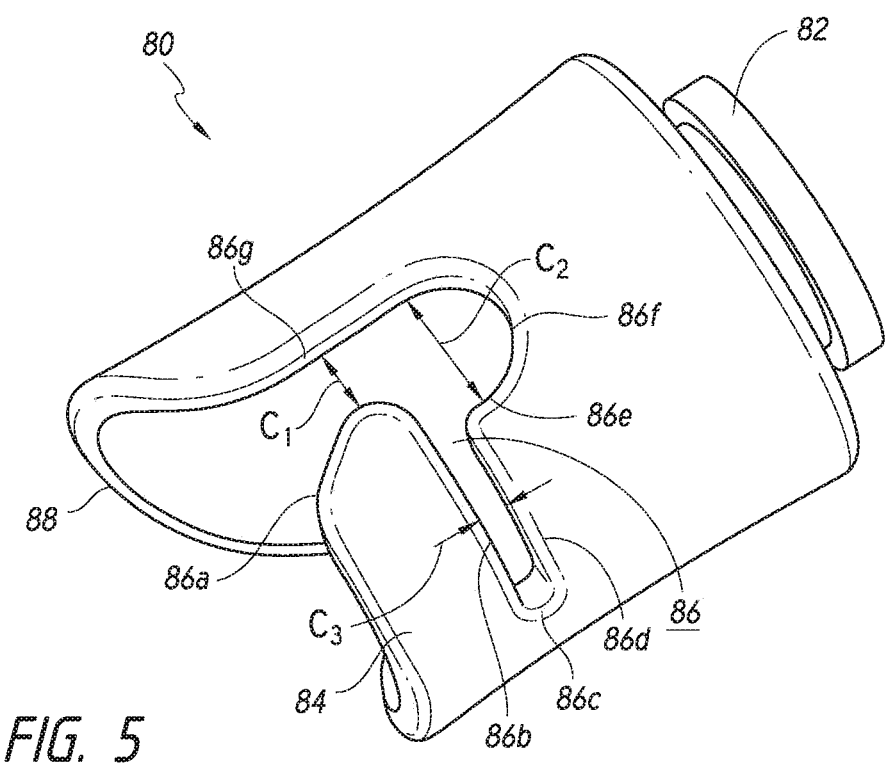
FIG. 5 illustrates another embodiment of a sheath adapter that can be used with the closure system shown in FIGS. 1A-1I.

FIG. 5 illustrates an enlarged view of another sheath adapter 80 that can be used with the closure system 20 to engage any sheath having a side port or irrigation line. The sheath adapter 80 can be integral with the handle portion 30 or a separate component coupled to the handle portion 30. As shown in FIG. 5, the sheath adapter 80 can include a proximal flange 82 to engage the handle portion 30.

As shown in FIG. 5, the sheath adapter 80 can have a generally cylindrical or generally frustoconical shape. The sheath adaptor 80 can include polycarbonate, ABS, silicone, an elastomer, or other suitable materials. An elastomeric material may be beneficial to enable the sheath adapter 40 to grip the side port 16 or irrigation line 12 of the sheath 10.

The sheath adapter 80 can include an attachment structure that can releasably attach to a procedural sheath, such as bayonet connector or hook portion 84. A distal facing edge 88 of the sheath adapter 80 can extend distally beyond the hook portion 84.

The hook portion 84 can form a passageway 86. The passageway 86 can be defined by a hook end edge 86a, a proximal facing edge 84b, a first inner lateral edge 86c, a first distal facing edge 86d, a second inner lateral edge 86e, a second distal facing edge 86f, and an outer lateral edge 86g. The edges defining the passageway 86 can be generally straight or curved.

The hook end edge 86a can be tapered inward toward the passageway 86 to guide the side port 16 or irrigation line 12 toward the passageway 86. A distance $C_1$ between the hook end edge 86a and the outer lateral edge 86g can be sized to prevent the side port 16 or irrigation line 12 from inadvertently exiting the passageway 86. The hook portion 84 can be a spring-member that can be deflected away from the central axis of the sheath adapter 80 to enlarge $C_1$ to permit passage of the side port 16 or irrigation line 12 into the passageway 106. After the side port 16 or irrigation line 12 is positioned in the passage 86, the hook portion 84 can return to its original state such that the side port 16 or irrigation line 12 is retained between the proximal facing edge 86b and the second distal facing edge 86f.

The second distal facing edge 86e can be proximal to the first distal facing edge 86c and spaced apart from the first distal facing edge 86c by the second inner lateral edge 86e. The second distal facing edge 86e can be generally curved to guide the side port 16 or irrigation line 12 toward the inner lateral surface 86c. The distance $C_2$ between the second inner lateral edge 86e and the outer lateral edge 86g can be greater than the distance $C_1$ and sized to receive the side port 16 or irrigation line 12. In one aspect, $C_1$ can be about 0.126 inches and $C_2$ can be about 0.210 inches, however, other appropriate dimensions are possible.

A length of the proximal facing edge 86b and/or the first distal facing edge 86d can be sufficient to enable the hook portion 84 to deflect outward and enlarge the distance $C_1$ to permit passage of the side port 16 or the irrigation line 12. For example, the proximal facing edge 86b and/or the first distal facing edge 86d can extend around at least 20% of a circumference of the sheath adapter 80, at least about 30% of a circumference of the sheath adapter, at least about 40% of a circumference of the sheath adapter, or at least about 50% of a circumference of the sheath adapter 80. A length of the proximal facing edge 86b can be longer than a length of the first distal facing edge 86d.

Alternatively, a distance $C_3$, between the proximal facing edge 86b and the first distal facing edge 86d, can be sized to permit the side port 16 or irrigation line 12 to traverse the passageway 86. The distance $C_3$ can be within 10% or within about 20% of a diameter of the side port 16 or irrigation line 12. The distance $C_3$ can be less than the distance $C_1$.

Figure 6:
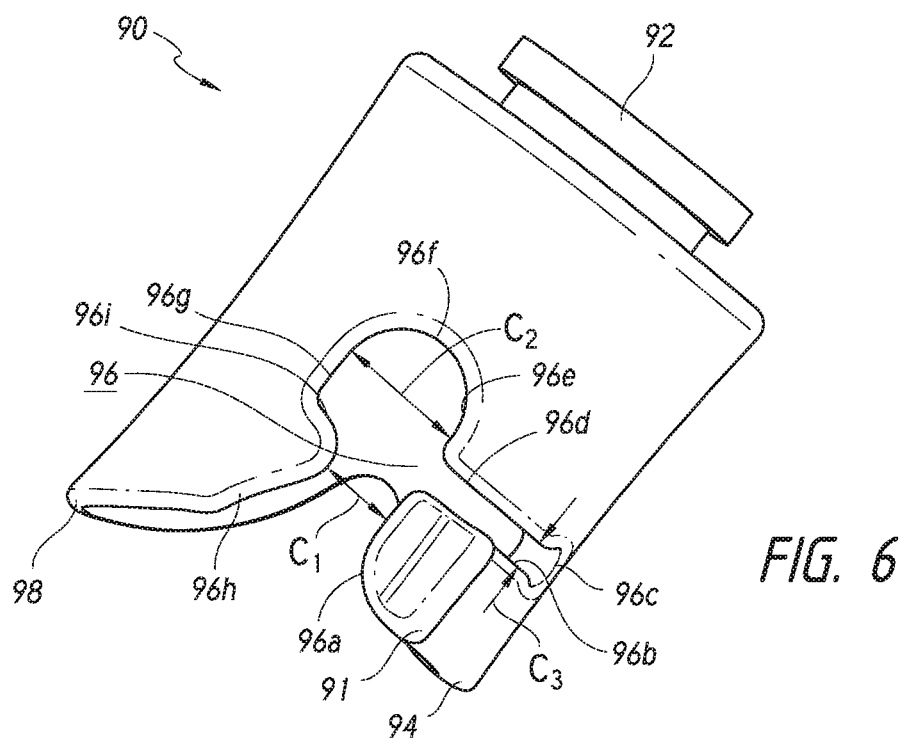
FIG. 6 illustrates another embodiment of a sheath adapter that can be used with the closure system shown in FIGS. 1A-1I.

FIG. 6 illustrates an enlarged view of another sheath adapter 90 that can be used with the closure system 20 to engage any sheath having a side port or irrigation line. The sheath adapter 90 resembles the sheath adapter 80 discussed above in many respects. Accordingly, numerals used to identify features of the sheath adapter 80 are incremented by a factor of one ten (10) to identify like features of the sheath adapter 90.

Unlike the sheath adapter 80, the hook end edge 96a of the sheath adapter 90 is generally straight and a distal section of the outer lateral edge 96h can be tapered inward to guide the side port 16 or irrigation line 12 into the passageway 96. The distal section of the outer lateral edge 96h and the proximal section of the outer lateral edge 96g are separated by a proximal facing step 96i.

The sheath adapter 90 can include a protruding portion or thumb grip 91 extending radially outward from the sheath adapter 90, which allows for the user to bend the hook end 96a outward away from the central axis of sheath adaptor 90 in order to enlarge $C_1$ and enable the removal of the sheath 10 from the sheath adaptor 90.

Figure 7:
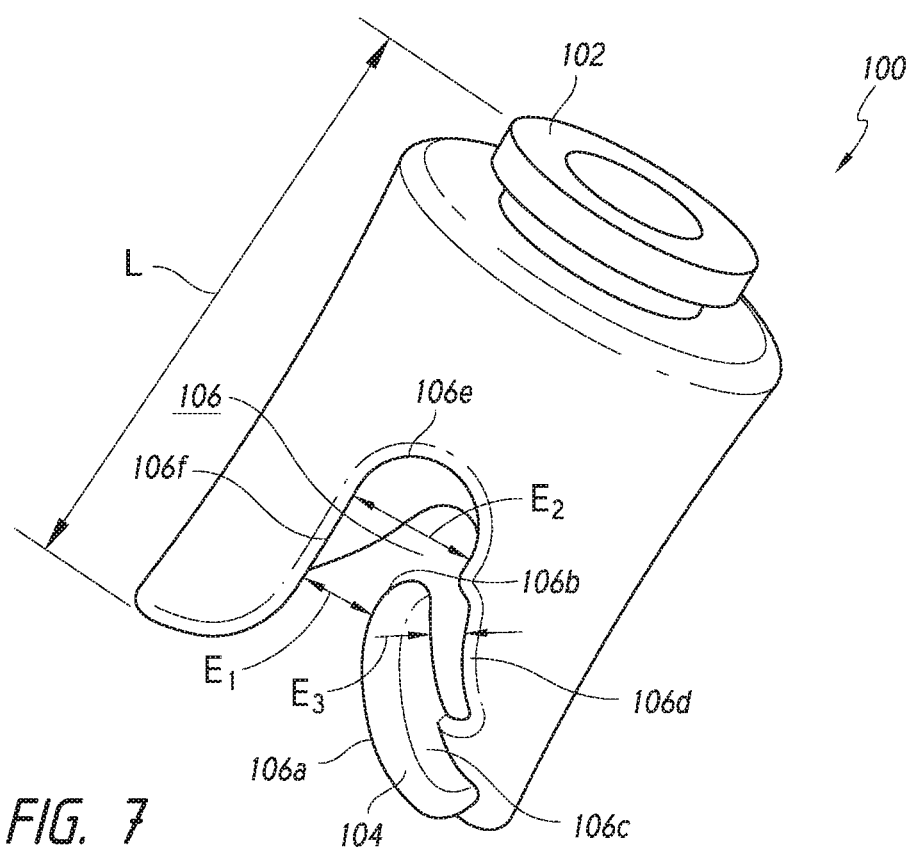
FIG. 7 illustrates another embodiment of a sheath adapter that can be used with the closure system shown in FIGS. 1A-1I.

FIG. 7 illustrates an enlarged view of another sheath adapter 100 that can be used with the closure system 20 to engage any sheath having a side port or irrigation line. The sheath adapter 100 can be integral with the handle portion 30 or a separate component coupled to the handle portion 30. As shown in FIG. 7, the sheath adapter 100 can include a proximal flange 102 to engage the handle portion 30. The proximal flange 102 may have a detent feature that permits the user to rotate the sheath adapter 100 for optimal positioning to accommodate side ports positioned at various angles, but prevent rotation of the sheath adaptor 100 during the procedure.

As shown in FIG. 7, the sheath adapter 100 can include an attachment structure that can releasably attach to a procedural sheath, such as a bayonet connector or hook portion 104. The hook portion 104 can protrude radially outward from the sheath adapter 100. The hook portion 104 can be shaped such that axial and rotational movement are required to disengage the sheath adapter 100 from the sheath 10. Alternatively the hook portion 104 may be configured such that it must be depressed to disengage the sheath adapter 100 from the sheath 10.

The hook portion 104 can form a passageway 106. The passageway 106 can be defined by a lower hook edge 106a, a hook end edge 106b, an upper hook edge 106c, an inner lateral edge 106d, a distal facing edge 106e, and an outer lateral edge 106f. The edges defining the passageway 106 can be generally straight or curved. The lower hook edge 106a can be generally tapered inward to guide the side port 16 or irrigation line 12 toward the passageway 106.

A distance $E_1$ between the hook end edge 106b and the outer lateral edge 106f can be sized to prevent the side port 16 or irrigation line 12 from inadvertently escaping the passageway 106. The hook portion 104 can be a spring-member that can be deflected toward the inner lateral edge 106d to decrease the distance $E_3$ and increase the distance $E_1$ to permit passage of the side port 16 or irrigation line 12 into the passageway 106. After the side port 16 or the irrigation line 12 is positioned in the passageway 106, the hook portion 104 can return to its original state such that the side port 16 or irrigation line 12 is retained between the distal facing edge 106e and the hook end edge 106b.

A length of the upper hook edge 106c can be sufficient to enable the hook portion 84 to deflect toward the inner lateral edge 106d and permit passage of the side port 16 or irrigation line 12 into the passageway 106. The length of the upper hook edge 106c can be sufficiently long to enable the hook end edge 106 to facilitate the retention of the side port 16 or irrigation line 12 and inhibit the sheath 10 from easily disengaging from the sheath adapter 100 when the closure system is rotated or pulled. For example, a length of the upper hook edge 106c can be at least about 20% of a length L of the sheath adapter 100, at least about 30% of a length L of the sheath adapter 100, or at least about 40% of a length L of the sheath adapter 100.

The distal facing edge 106e can be generally curved to guide the side port 16 or irrigation line 12 toward the portion of the passageway 106 between the upper hook edge 106c and the inner lateral edge 106d. The distance $E_2$ between the inner lateral edge 106d and the outer lateral edge 106f can be greater than the distance $E_1$. In one aspect, $E_1$ can be about 0.115 inches and $E_2$ can be about 0.210 inches, however, other appropriate dimensions can be possible.

Figure 8:
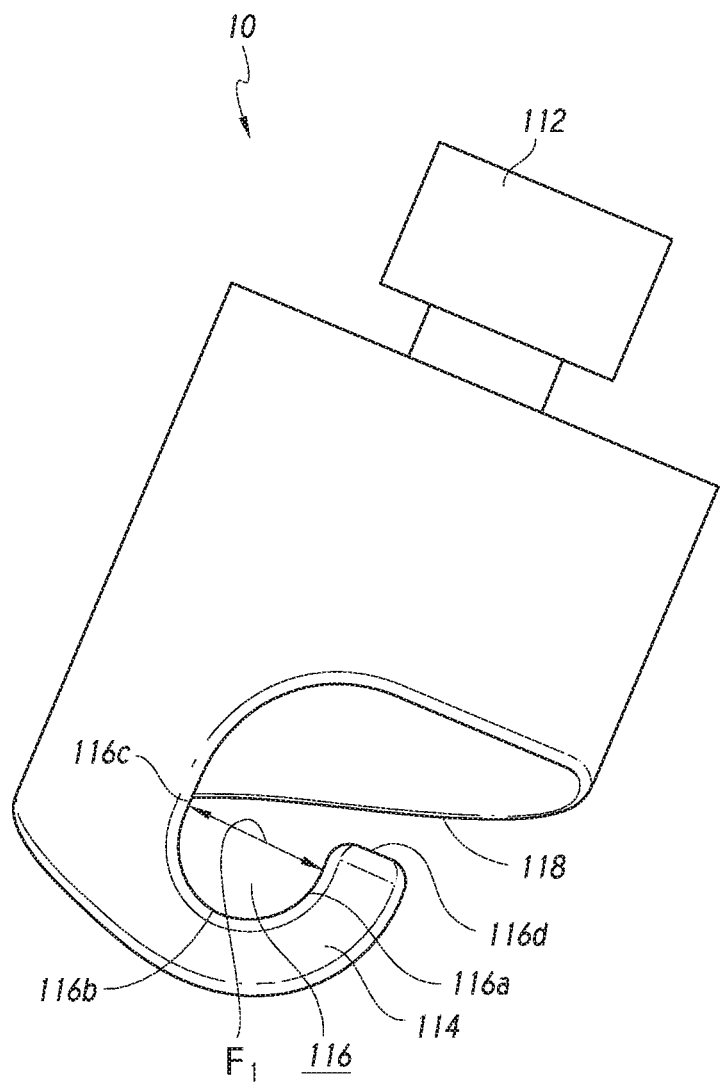
FIG. 8 illustrates another embodiment of a sheath adapter that can be used with the closure system shown in FIGS. 1A-1I.

FIG. 8 illustrates another sheath adapter 110 that can engage any sheath having a side port 16 or irrigation line 12. The sheath adapter 110 can be integral with the handle portion 30 or include a proximal flange 112 to engage the handle portion 30.

As shown in FIG. 8, the sheath adapter 110 that can have a generally cylindrical or generally frustoconical shape. The sheath adaptor 110 can include polycarbonate, ABS, silicone, and elastomer or other suitable materials. An elastomeric material may be beneficial to enable the sheath adapter 110 to grip the side port 16 or irrigation line 12 of the sheath 10.

The sheath adapter 110 can include an attachment structure that can releasably attach to a procedural sheath, such as a bayonet connector or hook portion 114 that can hook around the side port 16 or irrigation line 12 of a procedural sheath 10. The hook portion 116 can extend distally beyond a distal edge 118 of a remaining portion of the sheath adapter 110. The hook portion 114 can form a passageway 116 to retain the side port 16 or irrigation line 12. The hook portion 114 can be shaped such that both axial and rotational movement is required to disengage the hook portion 114 from the sheath 10.

The passageway 116 can be defined by an outer lateral edge 116a, a proximal facing edge 116b, an inner lateral edge 116c. The edges defining the passageway 116 can be generally straight or curved. The distance $F_1$ between the outer lateral edge 116a and the an inner lateral edge 116c can be sized to permit the side port 16 or irrigation line 12 to enter the passageway 116. For example, the distance $F_1$ can be within about 10% or within about 20% of a diameter of the side port 12 or the irrigation line 12. In one aspect, $F_1$ can be about 0.200 inches, however, other appropriate dimensions are possible.

In some embodiments, the distance $F_1$ can narrow from the proximal facing edge 116b toward the hook end edge 116d. The hook portion 114 can be spring-like and move away from the inner lateral edge 116c to enlarge the distance $D_1$ between the outer lateral edge 116a and inner lateral edge 116c to permit the side port 16 or irrigation line 12 to move toward the proximal facing edge 116b. The hook portion 114 can rebound back toward the inner lateral edge 116c to retain the side port 16 or irrigation line 12.

Although not shown, any of the sheath adapter embodiments can include barbs, threads, flanges, or other features to facilitate engagement with the sheath 10, for example, a snap fit or a friction fit. These features can be used to engage the side port, irrigation line, or outer or inner surface of the procedural sheath hub. The addition of any of these features can also be used to permanently couple any of the sheath adapters described above and the sheath 10.

Terminology

As used herein, the relative terms "proximal" and "distal" shall be defined from the perspective of the closure system. Thus, proximal refers to the direction of the handle of the closure system and distal refers to the direction of the distal tip of the closure system.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments, whether these features, elements, and/or steps are included or are to be performed in any particular embodiment.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount, as the context may indicate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 10 percent" includes "10 percent."

Any methods disclosed herein need not be performed in the order recited. The methods disclosed herein include certain actions taken by a practitioner; however, they can also include any third-party instruction of those actions, either expressly or by implication. For example, actions such as "tamping the sealant" include "instructing tamping of the sealant."

Although certain embodiments and examples have been described herein, it will be understood by those skilled in the art that many aspects of the closure system shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

The invention claimed is:

1. A closure system for closing a puncture in a vessel wall, the closure system comprising:
    an inner catheter having an expandable structure at a distal end thereof;
    a sealant positioned proximal to the expandable structure;
    a support tube proximal to the sealant;
    a handle portion at a proximal end of the inner catheter, the handle portion having an actuator configured to bend a portion of the inner catheter and retract the expandable structure proximally, wherein the actuator includes an arm configured to engage with the inner catheter to bend the inner catheter away from a central axis of the handle portion, thereby causing the expandable structure to retract into the support tube.

2. The closure system of claim 1, wherein the handle portion further comprises a lockout mechanism configured to prevent the actuator from being actuated when the expandable structure is in an expanded state.

3. The closure system of claim 1, wherein the handle portion further comprises an inflation indicator at a proximal end thereof, wherein the inflation indicator is configured to move from a first position to a second position when the expandable structure is fully expanded.

4. The closure system of claim 3, wherein in the second position the inflation indicator protrudes from the proximal end of the handle portion.

5. The closure system of claim 3, wherein the inflation indicator provides a lockout mechanism configured to prevent the actuator from being actuated when the expandable structure is in an expanded state.

6. The closure system of claim 5, wherein the lockout mechanism comprises a plurality of protrusions on the inflation indicator, the plurality of protrusions being configured to prevent the actuator from being depressed when the expandable member is in an expanded state, and wherein the protrusions shift distally when the expandable structure is deflated.

7. The closure system of claim 1, further comprising a sheath adapter having an attachment structure, wherein the attachment structure defines a passageway for releasable attachment to a procedural sheath by positioning a side port or an irrigation line of the procedural sheath into the passageway of the attachment structure.

8. A closure system for closing a puncture in a vessel wall, the closure system comprising:
    an inner catheter having an expandable structure at a distal end thereof;
    a sealant positioned proximal to the expandable structure;
    a support tube proximal to the sealant;
    a handle portion at a proximal end of the inner catheter, the handle portion having an actuator configured to bend a portion of the inner catheter and retract the expandable structure proximally, wherein the handle portion further comprises an inflation indicator at a proximal end thereof, wherein the inflation indicator is configured to move from a first position to a second position when the expandable structure is fully expanded and wherein the inflation indicator provides a lockout mechanism configured to prevent the actuator from being actuated when the expandable structure is in an expanded state.

9. The closure system of claim 8, wherein in the second position the inflation indicator protrudes from the proximal end of the handle portion.

10. The closure system of claim 8, wherein the lockout mechanism comprises a plurality of protrusions on the inflation indicator, the plurality of protrusions being configured to prevent the actuator from being depressed when the expandable member is in an expanded state, and wherein the protrusions shift distally when the expandable structure is deflated.

11. The closure system of claim 8, wherein the actuator includes an arm configured to engage with the inner catheter to bend the inner catheter away from a central axis of the handle portion, thereby causing the expandable structure to retract into the support tube.

12. The closure system of claim 8, further comprising a sheath adapter having an attachment structure, wherein the attachment structure defines a passageway for releasable attachment to a procedural sheath by positioning a side port or an irrigation line of the procedural sheath into the passageway of the attachment structure.

* * * * *